(12) United States Patent
Imai et al.

(10) Patent No.: US 12,383,290 B2
(45) Date of Patent: *Aug. 12, 2025

(54) MEDICAL DEVICE AND PROCEDURE METHOD

(71) Applicant: TERUMO KABUSHIKI KAISHA, Tokyo (JP)

(72) Inventors: Masaomi Imai, Kofu (JP); Takahiro Chida, Kawasaki (JP); Yuki Masubuchi, Hadano (JP); Takashi Kitaoka, Hadano (JP); Kazuaki Kanamoto, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,204

(22) Filed: Jun. 19, 2023

(65) Prior Publication Data

US 2023/0329735 A1 Oct. 19, 2023

Related U.S. Application Data

(63) Continuation of application No. 17/382,438, filed on Jul. 22, 2021, now Pat. No. 11,690,638, which is a
(Continued)

(30) Foreign Application Priority Data

Aug. 29, 2016 (JP) .................................. 2016-166617

(51) Int. Cl.
*A61F 2/01* (2006.01)
*A61B 17/22* (2006.01)
(Continued)

(52) U.S. Cl.
CPC ............ *A61B 17/221* (2013.01); *A61B 17/22* (2013.01); *A61F 2/0105* (2020.05);
(Continued)

(58) Field of Classification Search
CPC .................. A61B 17/221; A61B 17/22; A61B 2017/22084; A61B 2017/2212;
(Continued)

(56) References Cited

U.S. PATENT DOCUMENTS 7,780,696 B2   8/2010   Daniel et al.
RE42,983 E    11/2011   Kusleika
(Continued)

FOREIGN PATENT DOCUMENTS

JP   2007527264 A   9/2007
JP   2013027593 A   2/2013
(Continued)

OTHER PUBLICATIONS

Office Action (Notice of Reasons for Refusal) issued Jan. 30, 2023, by the Japan Patent Office in corresponding Japanese Patent Application No. 2022-066134 and an English Translation of the Office Action. (8 pages).
(Continued)

*Primary Examiner* — Kelly J Bekker
*Assistant Examiner* — Lindsey R. Rivers
(74) *Attorney, Agent, or Firm* — BUCHANAN INGERSOLL & ROONEY PC

(57) ABSTRACT

A medical device insertable into a blood vessel for effectively removing an object flowing in a biological lumen while reducing the burden on the living body includes an elongated shaft portion, and an expansion portion which is an elastically deformable cylindrical body having a plurality of gaps and in which a proximal portion or a distal portion of the cylindrical body is interlocked with the shaft portion.
(Continued)

The expansion portion has a ring-shaped or annular bent portion which protrudes toward a proximal side position radially outside the expansion portion in a bent state of being bent along an axial direction, and an axial length of a second portion from the bent portion to a proximal end of the expansion portion is shorter than an axial length of a first portion from the bent portion to the distal end of the expansion portion.

16 Claims, 15 Drawing Sheets

Related U.S. Application Data continuation of application No. 16/282,436, filed on Feb. 22, 2019, now Pat. No. 11,096,705, which is a continuation of application No. PCT/JP2017/030309, filed on Aug. 24, 2017.

(51) Int. Cl.
*A61B 17/221* (2006.01)
*A61B 17/3207* (2006.01)

(52) U.S. Cl.
CPC ............ *A61F 2/0108* (2020.05); *A61F 2/012* (2020.05); *A61F 2/013* (2013.01); *A61B 2017/22084* (2013.01); *A61B 2017/2212* (2013.01); *A61F 2002/015* (2013.01); *A61F 2002/016* (2013.01)

(58) Field of Classification Search
CPC ..... A61B 2017/2215; A61B 2017/2217; A61F 2/01; A61F 2/013; A61F 2002/015; A61F 2002/016; A61F 2/0105; A61F 2/012; A61F 2/0108; A61F 2/0103; A61F 2/014; A61F 2/02
See application file for complete search history.

(56) References Cited

U.S. PATENT DOCUMENTS

| 2002/0173819 | A1  | 11/2002 | Leeflang et al. |
| 2003/0176884 | A1* | 9/2003  | Berrada ................. A61F 2/0105 606/200 |
| 2005/0004594 | A1  | 1/2005  | Nool et al. |
| 2006/0100662 | A1* | 5/2006  | Daniel ................. A61B 17/221 606/200 |
| 2007/0233174 | A1* | 10/2007 | Hocking ............... A61F 2/0105 606/200 |
| 2007/0233175 | A1* | 10/2007 | Zaver .................... A61F 2/0105 606/200 |
| 2011/0054514 | A1* | 3/2011  | Arcand .................. A61F 2/013 29/428 |
| 2011/0125181 | A1* | 5/2011  | Brady .............. A61B 17/22031 606/200 |
| 2016/0113662 | A1  | 4/2016  | Kobayashi et al. |
| 2016/0331506 | A1  | 11/2016 | Korkuch et al. |
| 2019/0183519 | A1  | 6/2019  | Imai et al. |
| 2021/0346041 | A1  | 11/2021 | Imai et al. |

FOREIGN PATENT DOCUMENTS

| WO | 0053120    | A1 | 9/2000  |
| WO | 2011128934 | A1 | 10/2011 |
| WO | 2015079401 | A2 | 6/2015  |
| WO | 2016061373 | A1 | 4/2016  |
| WO | 2016067646 | A1 | 5/2016  |

OTHER PUBLICATIONS

The extended European Search Report issued Jan. 15, 2020, by the European Patent Office in corresponding European Patent Application No. 17846287.5-1113. (8 pages).
International Search Report (PCT/ISA/210) mailed on Oct. 31, 2017, by the Japanese Patent Office as the International Searching Authority for International Application No. PCT/JP2017 /030309.
Written Opinion (PCT/ISA/237) mailed on Oct. 31, 2017, by the Japanese Patent Office as the International Searching Authority for International Application No. PCT/JP2017/030309.

* cited by examiner

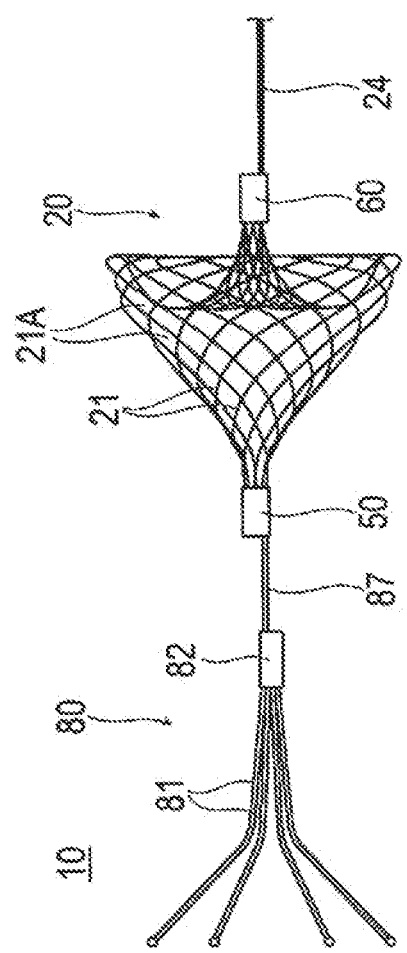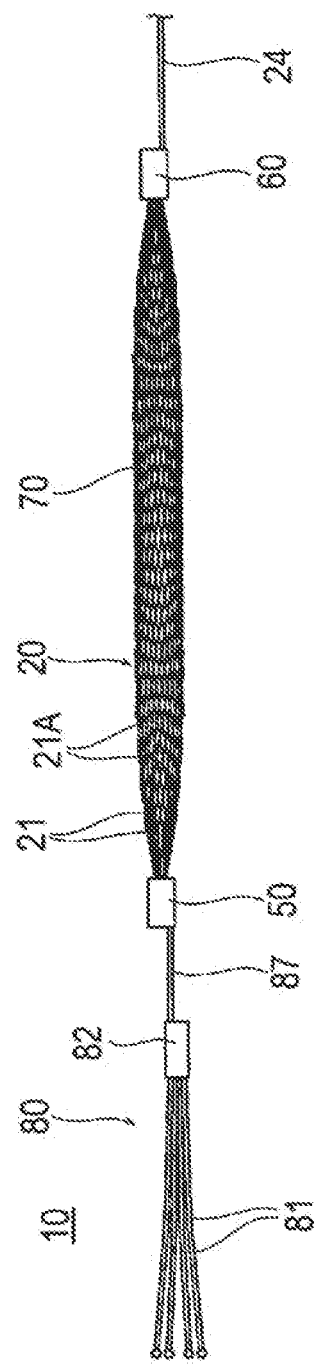
FIG. 3(A)
FIG. 3(B)

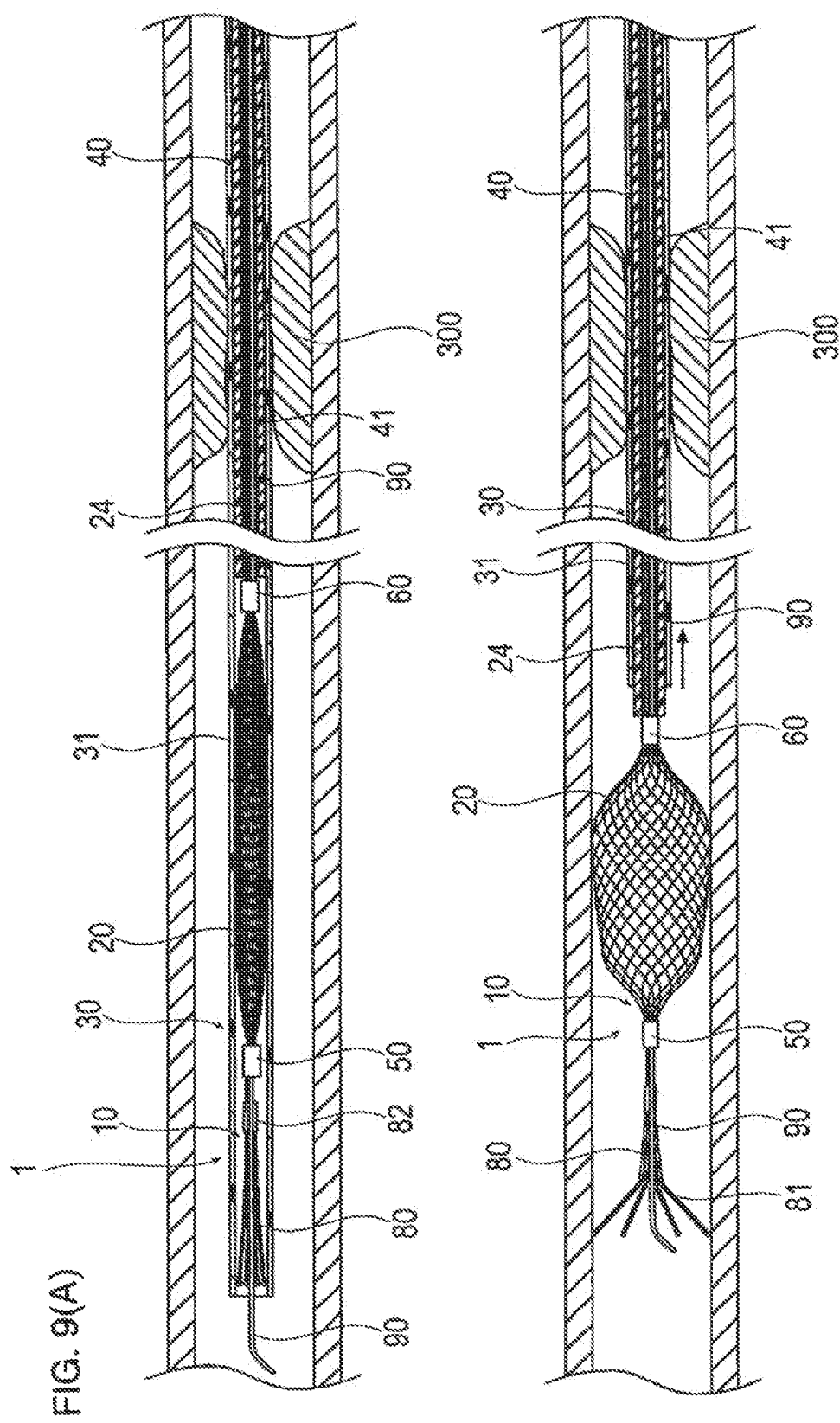

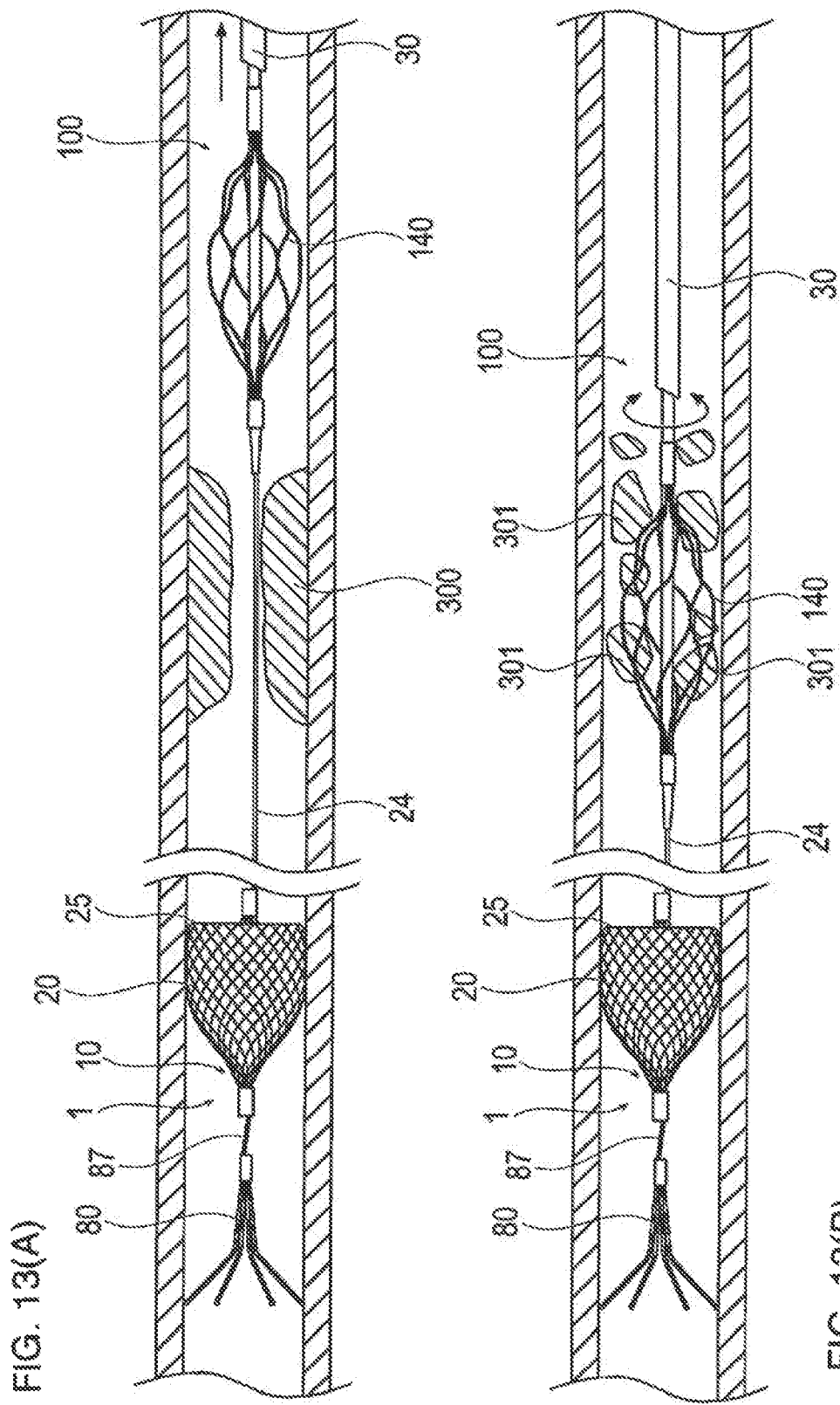

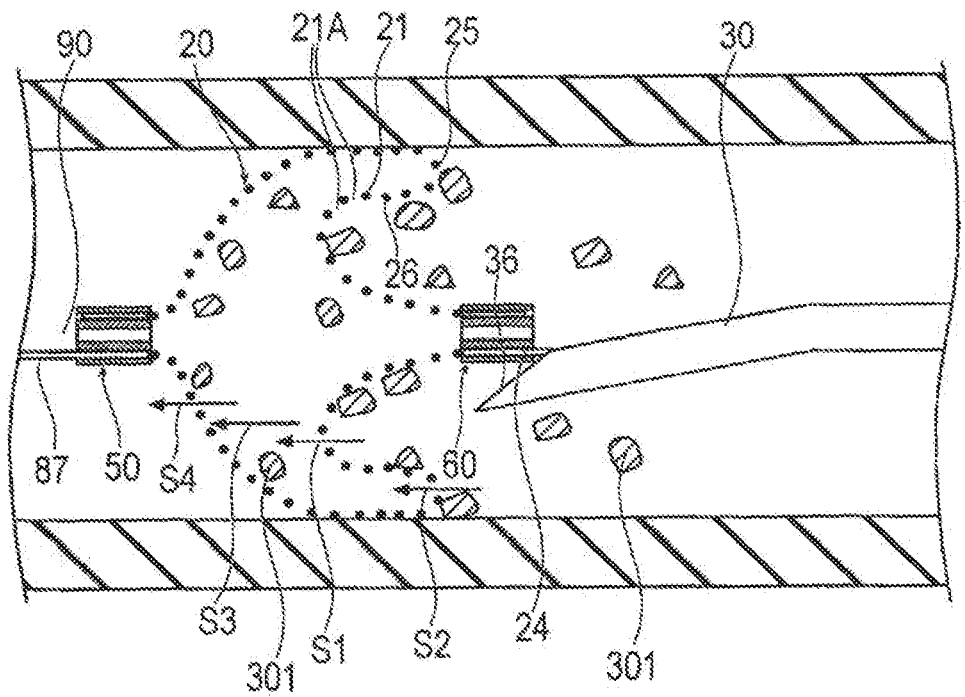
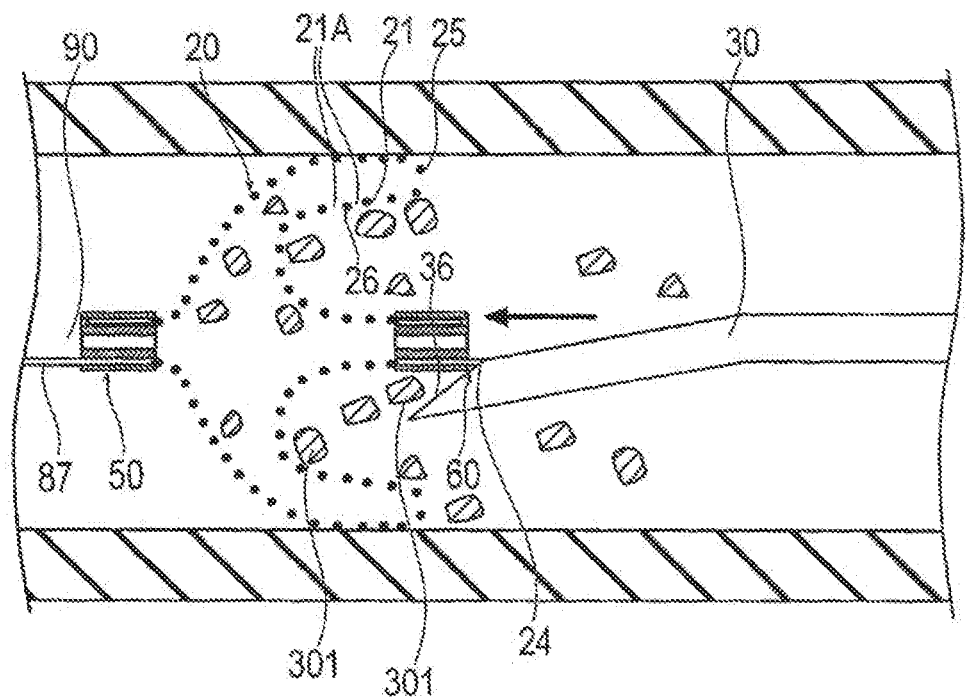

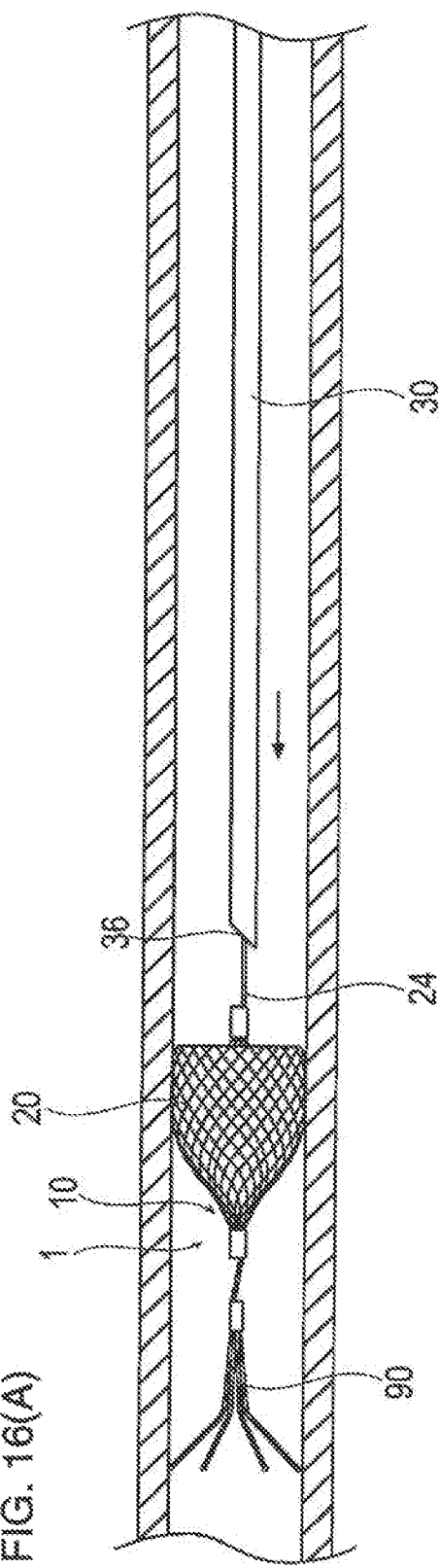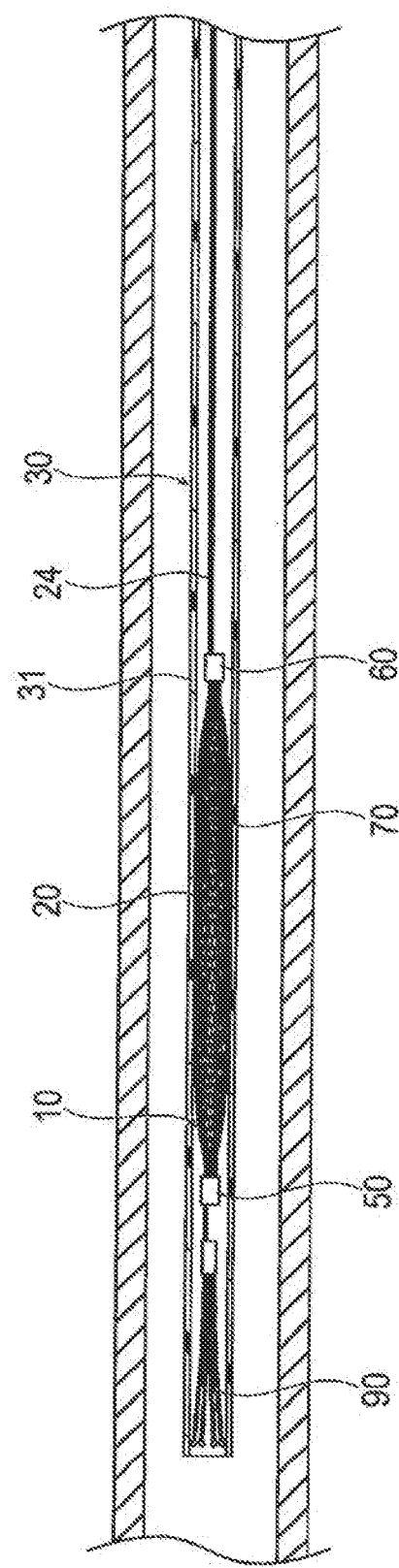

MEDICAL DEVICE AND PROCEDURE METHOD

CROSS-REFERENCES TO RELATED APPLICATIONS

This application is a continuation of U.S. patent application Ser. No. 17/382,438, filed Jul. 22, 2021, which is a continuation of U.S. patent application Ser. No. 16/282,436, filed Feb. 22, 2019, issued as U.S. Pat. No. 11,096,705 on Aug. 24, 2021, which is a continuation of International Application No. PCT/JP2017/030309 filed on Aug. 24, 2017, which claims priority to Japanese Application No. 2016-166617 filed on Aug. 29, 2016, the entire content of all four of which is incorporated herein by reference.

TECHNICAL FIELD

The present invention generally relates to a medical device to be inserted into a biological lumen and a procedure or method using a medical device.

BACKGROUND ART

A thrombus partially clogging a vein may, for example, cause pain and swelling. For the treatment, there is a method of percutaneously inserting a device and physically breaking and removing the thrombus. In such a treatment, if the thrombus completely or partially separated from the blood vessel wall travels in the blood stream and reaches the lungs, there is a risk of pulmonary embolism. Accordingly, when performing such a treatment, a thrombolytic agent may be used before and after the treatment and/or during the treatment, or the separated thrombus may be aspirated and removed as much as possible during the treatment. However, even though such a procedure is taken, there is a possibility that the separated thrombus having a chronically problematic size may reach the lungs and the like.

In order to avoid such pulmonary embolism, there is a method of indwelling a filter for collecting the thrombus flowing in the blood vessel in the blood vessel. For example, U.S. Reissue Pat. No. 42,983 discloses a device in which a filter in which linear bodies are knitted into a tubular shape is provided at a distal portion of a long extending wire. The filter pushes a proximal portion into an inner side of a distal portion and turns it back in an axial direction, so that the doubly contacted linear bodies can be formed into a cup shape as a whole.

SUMMARY

When a filter is disposed in the blood vessel, the thrombus is pushed and sticks to the filter by the fast blood stream. When the thrombus sticks to the filter, the flow of the blood is restricted, which is undesirable.

The medical device and procedure or method disclosed here is able to effectively collect an object flowing in the biological lumen.

The disclosed medical device to be inserted into a biological lumen for collecting an object in the biological lumen includes an elongated shaft possessing a distal end portion, and an expansion portion that includes an elastically deformable body, the elastically deformable body possessing a proximal portion and a distal portion, with the elastically deformable body including a plurality of through gaps that pass through the elastically deformable body. The proximal portion of the elastically deformable body is interlocked with a proximal side interlock portion, and the proximal side interlock portion includes a lumen extending throughout the proximal side interlock portion. The proximal side interlock portion is fixed to the distal end portion of the elongated shaft so that the elongated shaft and the proximal side interlock portion move together as a unit whereby movement of the elongated shaft results in movement of the proximal side interlock portion, and the elongated shaft extending away from the elastically deformable body in a proximal direction. The expansion portion includes, when the expansion portion is in a bent state, a radially outwardly located annular-shaped portion that is bent toward the proximal direction, and the expansion portion is changeable between the bent state and an extended state. The expansion portion in the bent state includes a first portion and a second portion, with the second portion being located inside the first portion when the expansion portion is in the bent state. The second portion moves in the proximal direction with respect to the first portion and is pulled out from the inside of the first portion when the expansion portion changes from the bent state to the extended state.

A procedure for collecting an object generated in a lesion area in a biological lumen includes: inserting a sheath in which the expansion portion is accommodated in a contracted state into the biological lumen; pushing out the expansion portion from the sheath on a downstream side from the lesion area of the biological lumen, expanding the expansion portion by an elastic force of the expansion portion, and indwelling the expansion portion in a biological lumen; shifting the expansion portion from the contracted state to a bent state; and collecting the object in the biological lumen by the expansion portion.

In the medical device and the procedure as described above, when the expansion portion is in the bent state, the first portion and the second portion hardly contact each other so that a space is formed between the first portion and the second portion. Accordingly, the gap of the expansion portion can be appropriately maintained, and the object can be effectively collected by the expansion portion by suppressing the clogging.

According to another aspect, a medical device to be inserted into a biological lumen for collecting an object in the biological lumen comprises an elongated shaft possessing a distal end portion and an expansion portion that includes an elastically deformable body, with the elastically deformable body possessing a proximal portion and a distal portion, and the elastically deformable body including a plurality of through gaps that pass through the elastically deformable body. The proximal portion of the elastically deformable body is interlocked with a proximal side interlock portion, and the distal end portion of the elongated shaft is fixed in place relative to the elastically deformable body by way of the proximal side interlock portion so that the elongated shaft and the proximal side interlock portion move together as a unit whereby movement of the elongated shaft results in movement of the proximal side interlock portion. The elongated shaft extends away from the elastically deformable body in a proximal direction. The expansion portion includes, when the expansion portion is in a bent state, a radially outwardly located annular-shaped portion that is bent toward the proximal direction. The expansion portion is changeable between the bent state and an extended state, with the expansion portion in the bent state including a first portion and a second portion, and the second portion being located inside the first portion when the expansion portion is in the bent state. The second portion moves in the proximal direction with respect to the first portion and is pulled out from the inside of the first portion when the expansion portion changes from the bent state to the extended state. The elongated shaft is the only elongated shaft that is fixed in place relative to the elastically deformable body and that also extends away from the elastically deformable body in the proximal direction.

In accordance with a further aspect, a medical device to be inserted into a biological lumen for collecting an object in the biological lumen comprises: an elongated shaft possessing a distal end portion; and an expansion portion that includes an elastically deformable body having a plurality of through gaps that pass through the elastically deformable body, with the expansion portion possessing a proximal portion and a distal portion. The distal end portion of the elongated shaft is fixed to the proximal portion of the expansion portion and extends away from the expansion portion in a proximal direction. The expansion portion is changeable from an extended state to a bent state by a restoring force of the expansion portion and without application of any forces external to the expansion portion so that as the expansion portion changes form the extended state to the bent state, the expansion portion expands radially outwardly and an axial distance between the distal end portion of the expansion portion and the proximal end portion of the expansion portion is reduced. The expansion portion includes, when the expansion portion is in the bent state, a radially outwardly located annular-shaped portion that is bent toward the proximal direction, and the expansion portion in the bent state includes a first portion and a second portion, with the second portion being located inside the first portion when the expansion portion is in the bent state. The expansion portion is changeable from the bent state to an extended state, and the second portion moves in the proximal direction with respect to the first portion and is pulled out from the inside of the first portion when the expansion portion changes from the bent state to the extended state.

BRIEF DESCRIPTION OF THE DRAWINGS

FIGS. 3(A) and 3(B) are plane views showing an expansion portion of the expansion tool, with FIG. 3(A) showing an expanded state of the expansion portion, and FIG. 3(B) showing a contracted state of the expansion portion.

FIGS. 9(A) and 9(B) are cross-sectional views showing a state in a blood vessel, with FIG. 9(A) showing a state when the medical device is inserted into the blood vessel, and FIG. 9(B) showing a state when the expansion portion and an auxiliary expansion portion are expanded in the blood vessel.

FIGS. 13(A) and 13(B) are cross-sectional views showing a state in the blood vessel, with FIG. 13(A) showing an expanded state of a breaking member of the aspiration device, and FIG. 13(B) showing a state when a thrombus is broken by the expanded breaking member.

FIG. 14 is a cross-sectional view showing a state in which the broken thrombus is collected by the expansion portion.

FIG. 15 is a cross-sectional view showing a state in which the expansion portion collecting the broken thrombus is deformed.

FIGS. 16(A) and 16(B) are cross-sectional views showing a state in the blood vessel, with FIG. 16(A) showing a state in which the breaking member is accommodated in the sheath, and FIG. 16(B) showing a state in which the expansion portion and the auxiliary expansion portion are accommodated in the sheath.

DETAILED DESCRIPTION

Set forth below with reference to the accompanying drawings is a detailed description of embodiments of a medical device and procedure/method representing examples of the inventive medical device and procedure/method disclosed here. The dimensions or scales on the drawings may be exaggerated or different from actuality/reality for convenience of description and illustration.

A medical device 1 according to one embodiment is used for partially suppressing the flow in the blood vessel in order to aspirate and remove an object such as a thrombus, plaque, a calcified lesion, and the like in the blood vessel. In the description below, a side of the device inserted into the blood vessel is referred to as a "distal side" or "distal end", and a hand-side to be operated is referred to as a "proximal side" or "proximal end". Moreover, the object to be removed is not necessarily limited to a thrombus, plaque, or a calcified lesion, and may correspond to any object that can exist in the biological lumen. Moreover, in the present specification, a source side of the blood flow in the blood vessel is referred to as an "upstream side", and a side where the blood flow is heading is referred to as "downstream side".

Figure 1:
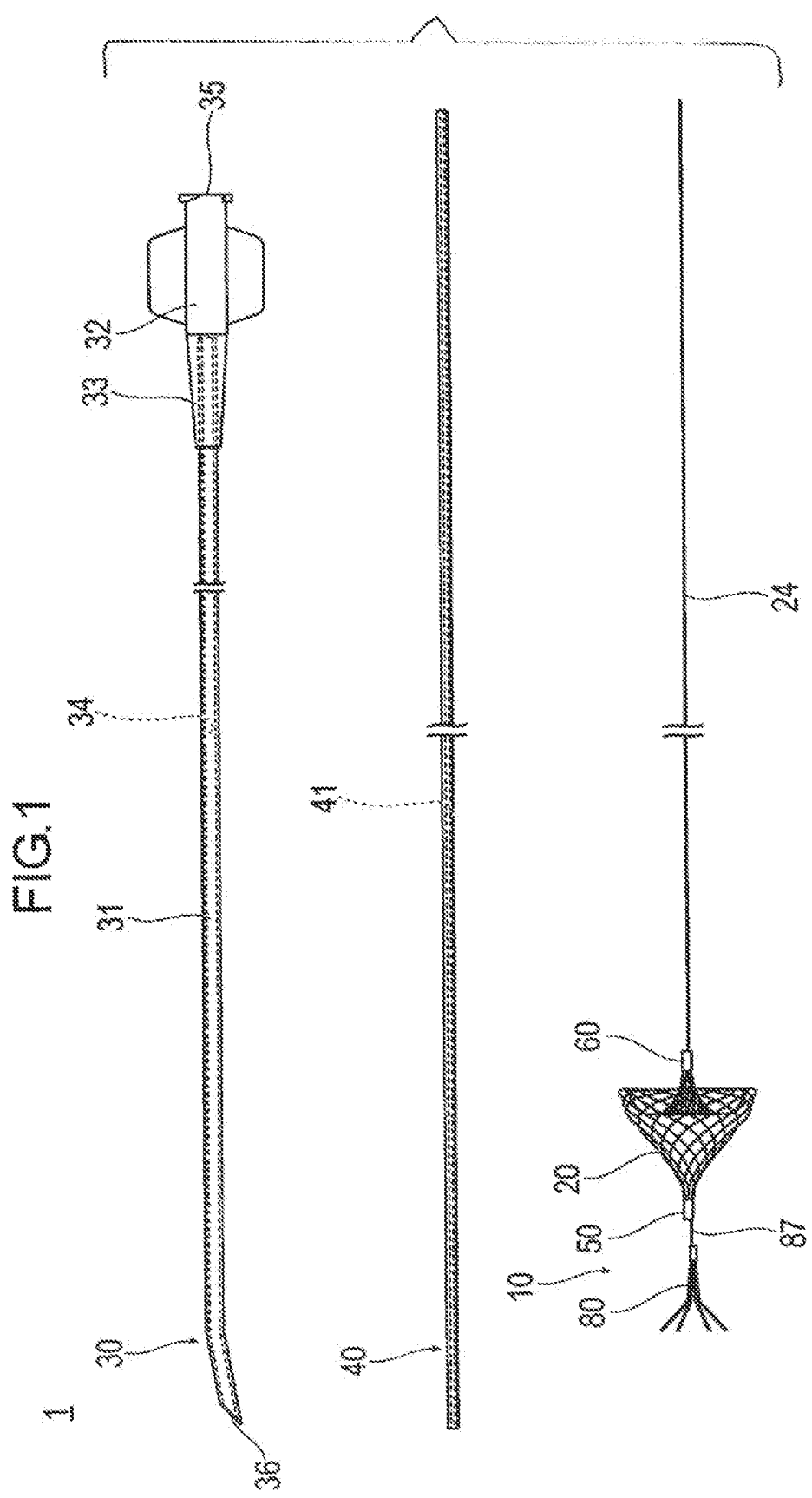
FIG. 1 is a plane view showing a medical device according to an embodiment.
Figure 2:
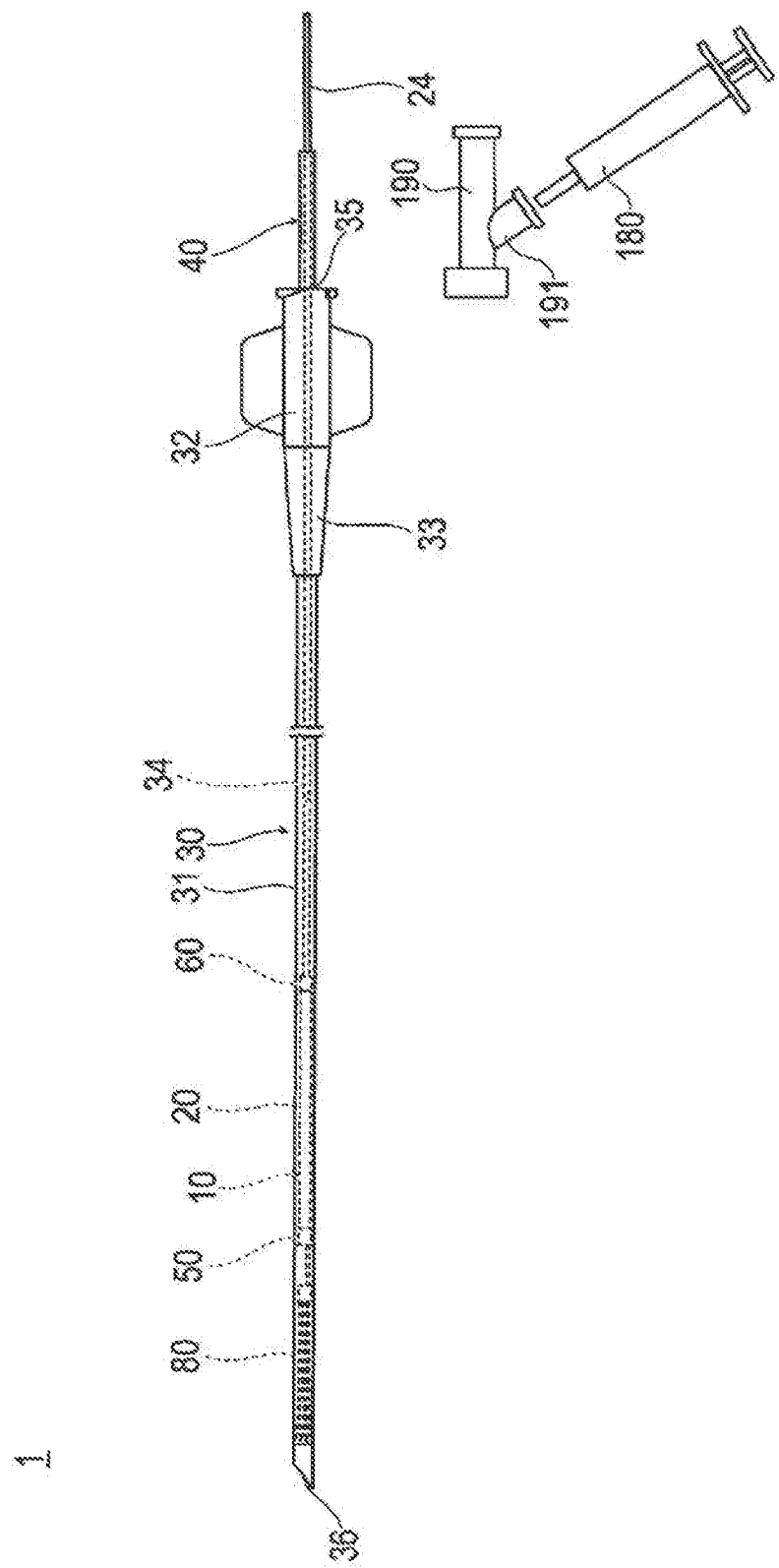
FIG. 2 is a plane view showing a state in which an expansion tool, a pressing shaft, and a sheath of the medical device according to the embodiment are combined.

As shown in FIGS. 1 and 2, the medical device 1 according to one embodiment representing an example of the disclosed medical device includes an expansion tool 10 for restricting the blood flow in the blood vessel, a sheath 30 configured to accommodate the expansion tool 10, and a pressing shaft 40 used for pushing out the expansion tool 10 from the sheath 30.

Figure 4:
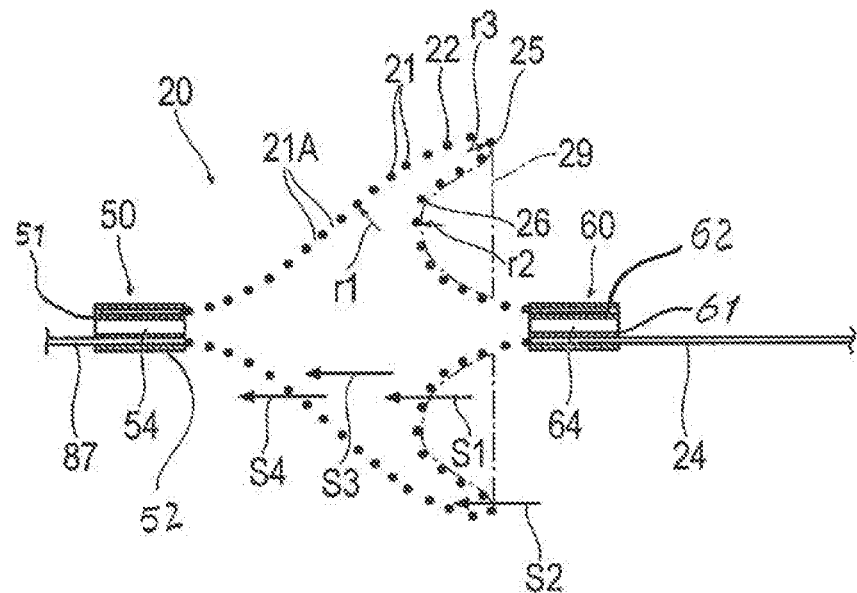
FIG. 4 is a cross-sectional view showing the expansion portion in a bent state.

As shown in FIGS. 3 and 4, the expansion tool 10 includes an expansion portion 20 which is a mesh-like cylindrical body having a plurality of gaps 21A that pass through the expansion portion 20, an elongated shaft portion 24 which is interlocked with the expansion portion 20 so that the two move together as a unit, and an auxiliary expansion portion 80 which is provided on the distal side from the expansion portion 20.

As shown in FIGS. 1, 3(A) and 3(B), the shaft portion 24 is an elongated shaft or elongated wire extending from a proximal end (operated or held by the user's hand) to the expansion portion 20. A distal end portion of the shaft portion 24 is connected to a proximal side interlock portion 60 of the expansion portion 20.

The constituent material of which the shaft portion 24 is fabricated is not particularly limited, but, for example, stainless steel, shape memory alloy, and the like can be suitably used.

As shown in FIGS. 3(A) and 3(B), the expansion portion 20 includes a plurality of flexibly and elastically deformable linear bodies 21 braided into a mesh shape so as to form a cylindrical body, a distal side interlock portion 50, and the proximal side interlock portion 60 interlocked with the shaft portion 24. The expansion portion 20 may be formed by braiding so that the gaps 21A exist between the plurality of linear bodies 21.

As shown in FIG. 4, the distal side interlock portion 50 includes an inner tube 51 located on the inner side of the linear bodies 21 and an outer tube 52 located on the outer side of the linear bodies 21. The distal end portion of the linear bodies 21 and a proximal end portion of an interlock shaft 87 are interposed and fixed between the inner tube 51 and the outer tube 52. The inner surface side of the inner tube 51 is a guide wire lumen 54 into which a guide wire can be inserted. The interlock shaft 87 is a shaft which interlocks the expansion portion 20 with the auxiliary expansion portion 80.

The proximal side interlock portion 60 includes an inner tube 61 located on the inner side of the linear bodies 21 and an outer tube 62 located on the outer side of the inner tube 61. The proximal end portion of the linear bodies 21 and the distal end portion of the shaft portion 24 are interposed and fixed between the inner tube 61 and the outer tube 62. Therefore, the proximal side interlock portion 60 is movable in the axial direction with the shaft portion 24. The inner surface side of the inner tube 61 is a guide wire lumen 64 into which the guide wire can be inserted.

In a natural state in which an external force is not applied, the expansion portion 20 is in a bent state (see FIG. 3(A)) of being bent in the axial direction while being expanded in outer diameter by the elastic force (restoring force) of the linear bodies 21. When the expansion portion 20 is in the bent state, the proximal side interlock portion 60 and the distal side interlock portion 50 approach each other. Moreover, the expansion portion 20 is accommodated in the sheath 30 (see FIGS. 1 and 2) while the expansion portion 20 is in a contracted state (see FIG. 3(B)) in which the expansion portion 20 is elastically deformed and the outer diameter of the expansion portion 20 is reduced. When the expansion portion 20 is in the contracted state, the proximal side interlock portion 60 and the distal side interlock portion 50 are separated from each other. The outer diameter of the braided expansion portion 20 can be changed by changing the distance between the proximal side interlock portion 60 and the distal side interlock portion 50.

The expansion portion 20 is indwelled in the blood vessel in a shape close to the natural state. In particular, the expansion portion 20 is indwelled in the blood vessel wall in a state of being contracted to a certain degree in the radial direction from the natural state so as to generate pressing force against the blood vessel wall by the expansion force of the expansion portion (see FIG. 11).

Figure 5:
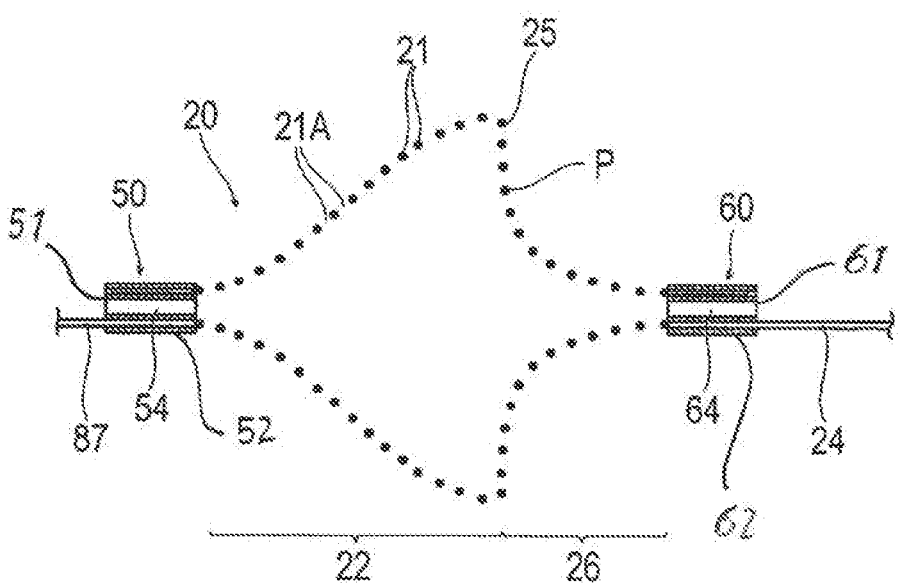
FIG. 5 is a cross-sectional view showing the expansion portion in a boundary state.

The expansion portion 20 includes a first portion 22 interlocked with the distal side interlock portion 50 and a second portion 26 interlocked with the proximal side interlock portion 60. In the bent state, the second portion 26 enters the inside of the first portion 22 (i.e., the first portion 22 overlies the second portion 26). That is, the expansion portion 20 is shaped in advance so as to have such a shape. The shaping can be carried out, for example, by holding it in a predetermined shape, accommodating it in a mold, and heating it. The inside of the expansion portion 20 is a region surrounded by the inner surface of the expansion portion 20. The inner surface of the expansion portion 20 means the inner surface of the cylindrical body formed by braiding the linear bodies 21. At this time, as shown in FIGS. 4 and 5, the linear bodies 21 located on the distal side of the expansion portion 20 form the concave-shaped first portion 22 which opens to the proximal side. The linear bodies 21 located on the proximal side of the expansion portion 20 form the concave-shaped second portion 26, and the concave shape opens to the proximal side on the inner surface side of the first portion 22. The first portion 22 and the second portion 26 are interlocked with each other by a bent portion 25 constituting an end portion on the proximal side of the expansion portion 20. Thereby, the second portion 26 on the proximal side of the expansion portion 20 is located on the inside of the first portion 22 on the distal side, and the expansion portion 20 is in the bent state of being bent in the axial direction. The second portion 26 has a concave shape which opens to the proximal side, and forms an inner space 29 on the inner side of the concave shape. The inner space 29 is a ring-shaped or annular space located on the distal side from the bent portion 25. In the bent state, the first portion 22 and the second portion 26 are separated from each other without coming into contact with each other. Accordingly, a space is formed between the first portion 22 and the second portion 26.

In the bent state, the first portion 22 and the second portion 26 have different shapes. Accordingly, the first portion 22 and the second portion 26 are able to be separated from each other without coming into contact with each other. Accordingly, a space is formed between the first portion 22 and the second portion 26. That is, as shown in FIG. 4, in the bent portion of the expansion portion, one part of the linear bodies 21 constituting the first portion 22 of the expansion portion axially overlaps another part of the linear bodies 21 constituting the second portion 26 of the expansion portion, and the two axially overlapping parts of the linear bodies are radially spaced from one another. Moreover, in the bent state, the axial length of the second portion 26 is shorter than the axial length of the first portion 22. Accordingly, a space is easily formed between the first portion 22 and the second portion 26. FIG. 3(A) and FIG. 4 show that the expansion portion 20 in the bent state includes a radially outwardly located annular portion defined by spaced apart parts of the first portion 22 and the second portion 26 that face one another, and this radially outwardly located annular portion is bent in the axial direction toward the proximal direction. The expansion portion 20 is thus configured to be positioned in the bent state in which a portion of the expansion portion 20 is the bent portion that is bent back upon itself as a result of parts or opposite ends of the expansion portion 20 that are spaced apart from one another in the axial direction being relatively moved towards one another in the axial direction.

It is preferable that the first portion 22 and the second portion 26 already have different shapes in a state before the shaping processing. Accordingly, by the shaping processing, the first portion 22 and the second portion 26 can have different shapes with high accuracy.

In the bent state, the proximal side interlock portion 60 is located on the proximal side from the bent portion 25. That is, the proximal side interlock portion 60 is not located in the inner space 29. Accordingly, the expansion portion 20 extends to the proximal side from the bent portion 25. Accordingly, an area of the expansion portion 20 functioning as a filter can be increased. The proximal side interlock portion 60 may be located on the distal side from the bent portion 25.

In a cross section of the expansion portion 20 along the axial direction, a curvature radius r1 of a portion convex toward the distal side of the first portion 22 is larger than a curvature radius r2 of a portion convex toward the distal side of the second portion 26. Accordingly, the second portion 26 tends to be shorter than the first portion 22 in the axial direction. Accordingly, the first portion 22 and the second portion 26 are separated from each other without coming into contact with each other, and a space between the first portion 22 and the second portion 26 is secured. The curvature radius r1 is appropriately set, but is, for example, 1 to 100 cm, preferably 4 to 30 cm, and more preferably 5 to 20 cm. The curvature radius r2 is appropriately set, but is, for example, 0.01 to 10 cm, preferably 0.05 to 8 cm, and more preferably 0.1 to 4 cm. The curvature radius r1 may be equal to or less than the curvature radius r2.

In the bent state, the bent portion 25 is located on the proximal side of the first portion 22 and the second portion 26. The bent portion 25 interlocks the first portion 22 with the second portion 26. In the bent state, the bent portion 25 is a ring-shaped portion which protrudes toward the proximal side and is the radially outermost part of the expansion portion 20. The gaps 21A of the bent portion 25 are narrower or smaller than the gaps in the first portion 22 and the second portion 26. Accordingly, the linear bodies 21 of the bent portion 25 are dense, and the repulsive force of the linear bodies 21 is high in the bent portion 25, so that it is strongly fixed to or pressed against the blood vessel. Accordingly, the position of the expansion portion 20 is stabilized, and the expansion portion 20 can be easily bent.

In the bent state, a curvature radius r3 of a portion convex toward the proximal side of the bent portion 25 is appropriately set, but is, for example, 0.001 to 5 cm, preferably 0.001 to 3 cm, and more preferably 0.001 to 1 cm.

When the blood flowing in the blood vessel reaches the expansion portion 20 in a state in which the expansion portion 20 is indwelled in the blood vessel and the blood is flowing from the proximal side, the blood enters the inside of the expansion portion 20 from a first flow path S1 passing through the gaps 21A of the second portion 26 or a second flow path S2 passing through the gaps 21A of the bent portion 25. In the bent state, the inside of the expansion portion 20 is interposed between the first portion 22 and the second portion 26. When the bent portion 25 is bent, the linear bodies 21 are dense. Accordingly, the gaps 21A of the bent portion 25 are narrower than the gaps 21A of the second portion 26 and the first portion 22. The blood entering the inside of the expansion portion 20 from the first flow path S1 or the second flow path S2 flows a third flow path S3 between the first portion 22 and the second portion 26 in a distal direction. Thereafter, the blood passes through the expansion portion 20 to the distal side by a fourth flow path S4 passing through the gaps 21A of the first portion 22.

In the bent state, the distance between the proximal side interlock portion 60 and the distal side interlock portion 50 can be appropriately set. The distance between the proximal side interlock portion 60 and the distal side interlock portion 50 may vary depending on the applied inner diameter of the blood vessel. Moreover, in the middle of the procedure, the distance between the proximal side interlock portion 60 and the distal side interlock portion 50 may be changed.

Figure 7:
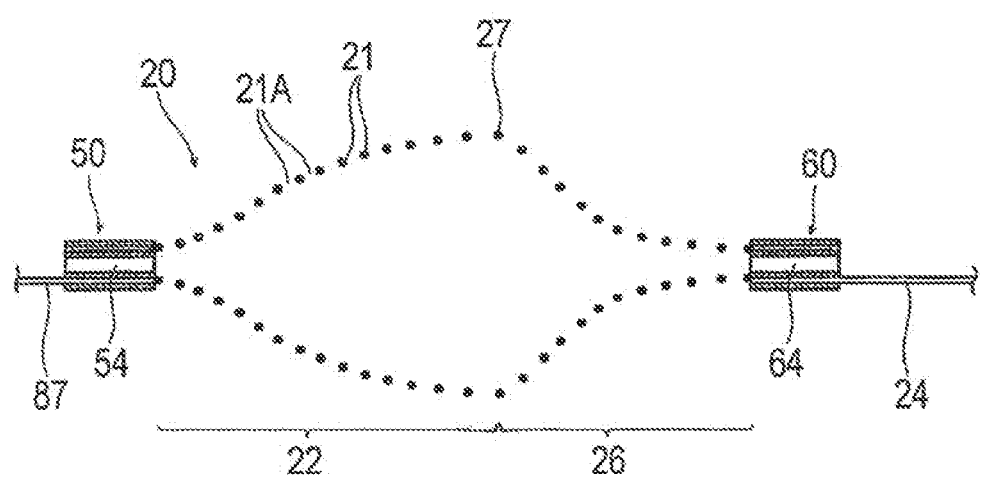
FIG. 7 is a cross-sectional view showing the expansion portion in an extended state.

When the proximal side interlock portion 60 and the distal side interlock portion 50 are gradually separated from each other from the bent state, as shown in FIG. 5, at some time, the second portion 26 is no longer located on the inside of the first portion 22. The state of the expansion portion 20 at this time is a boundary state. When the proximal side interlock portion 60 and the distal side interlock portion 50 are further separated from each other from the boundary state, as shown in FIG. 7, the entire second portion 26 is in an extended state of being located on the proximal side of the first portion 22. When the proximal side interlock portion 60 and the distal side interlock portion 50 are further separated from each other from the extended state, as shown in FIG. 3(B), the expansion portion 20 is in a contracted state. The contracted state is a state in which the expansion portion 20 can be accommodated in the sheath 30. In the bent state, boundary state, extended state, and contracted state, the axial length of the second portion 26 is shorter than the axial length of the first portion 22. The axial length of the second portion 26 may be equal to or longer than the axial length of the first portion 22 in any of the states.

Figure 6:
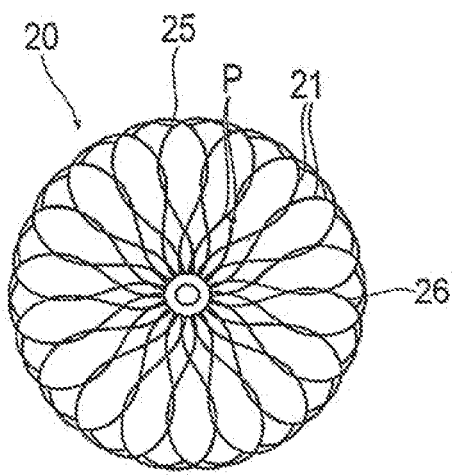
FIG. 6 is a plane view of linear bodies in the boundary state seen from an axial direction.

In the boundary state, as shown in FIGS. 5 and 6, the linear bodies 21 have inflection points P in the second portion 26 as seen from the axial direction of the expansion portion 20. That is, the bending direction of the linear bodies 21 is reversed at the inflection points P as a boundary. The linear bodies 21 are shaped to have the inflection points P. The inflection points of the linear bodies 21 are not provided in the first portion 22.

In the boundary state, when the linear bodies 21 have the inflection points P in the second portion 26, it is easier to turn back the expansion portion 20 using the inflection points P. Accordingly, it is easy to bring the expansion portion 20 in the extended state or the boundary state into the bent state.

When the expansion portion 20 is in the extended state, if the shaft portion 24 is moved to the distal side, as shown in FIG. 4, the proximal side interlock portion 60 is pushed into the distal side or toward the distal direction by the shaft portion 24. Thereby, the proximal side interlock portion 60 approaches the distal side interlock portion 50, so that the expansion portion 20 can be in the bent state of being bent in the axial direction. At this time, the fixing force of the auxiliary expansion portion 80 against the blood vessel is larger than the pushing force at the shaft portion 24. Thereby, when the proximal side interlock portion 60 is moved to the distal side, the proximal side interlock portion 60 can approach the distal side interlock portion 50 without the distal side interlock portion 50 being moved.

In the extended state, as shown in FIG. 7, the shapes of the second portion 26 and the first portion 22 are non-planar symmetric with respect to an axially orthogonal cross section (i.e., with respect to a cross-section taken along a plane that contains the central axis of the expansion portion and that is perpendicular to the plane of the paper). The second portion 26 and the first portion 22 are non-planar symmetric in that the cross-section of the first portion 22 is larger than the cross-section of the second portion 26. Note that, symmetry herein is related to a shape of the cylindrical body of the expansion portion 20 and also the size, but is not related to the disposition place of the plurality of linear bodies 21 constituting the expansion portion 20. If the shapes of the second portion 26 and the first portion 22 are planar symmetric (or substantially planar symmetric) with respect to the axially orthogonal cross section, the second portion 26 and the first portion 22 are likely to contact each other in the bent state. On the other hand, if the shapes of the second portion 26 and the first portion 22 are non-planar symmetric, the second portion 26 and the first portion 22 hardly contact each other. Thereby, when it obtains the bent state, an interval or space between the first portion 22 and the second portion 26 can be secured widely and reliably.

Moreover, in the extended state, a length from a portion 27 having a maximum outer diameter of the expansion portion 20 to the distal end of the expansion portion 20 is longer than a length from the portion 27 having the maximum outer diameter of the expansion portion 20 to the proximal end of the expansion portion 20. Accordingly, the axial length of the second portion 26 is shorter than the axial length of the first portion 22. Therefore, by obtaining the bent state, a space is easily formed between the first portion 22 and the second portion 26. Thereby, the interval between the first portion 22 and the second portion 26 can be secured widely and reliably.

Moreover, in the extended state, a maximum outer diameter of the second portion 26 is larger than a maximum outer diameter of the first portion 22. That is, the portion 27 having the largest outer diameter of the expansion portion 20 in the extended state is in the second portion 26. Accordingly, when the expansion portion 20 is in the bent state, the interval between the first portion 22 and the second portion 26 can be secured widely and reliably.

Moreover, in the extended state, a maximum inclination angle of the second portion 26 of the expansion portion 20 with respect to the axial direction is larger than the maximum inclination angle of the first portion 22 with respect to the axial direction. Accordingly, the second portion 26 tends to be bent in the axial direction and to be located in the inside of the first portion 22. Furthermore, since the first portion 22 and the second portion 26 have different shapes by obtaining the bent state, a space is easily formed between the first portion 22 and the second portion 26. Accordingly, the interval between the first portion 22 and the second portion 26 can be secured widely and reliably.

When the expansion portion 20 is in the bent state, when an interval between the first portion 22 and the second portion 26 can be secured widely and reliably, the first portion 22 and the second portion 26 do not contact each other. Thereby, the gaps 21A appropriate for the expansion portion 20 are secured. When the first portion 22 and the second portion 26 contact each other, the gaps 21A of the first portion 22 and the gaps 21A of the second portion 26 can directly communicate each other, so that the range where the appropriate gaps 21A are provided will be reduced. This will reduce the range where the expansion portion 20 appropriately functions as a filter, so that clogging can easily occur. On the other hand, as the range where the appropriate gaps 21A are provided is increased, the range where the expansion portion 20 appropriately functions as a filter is increased, so that clogging will be less likely to occur.

The shape of the second portion 26 in the extended state is different from the shape of the second portion 26 in the bent state, and is non-planar symmetric with respect to a cross section (axially orthogonal cross section) orthogonal to the central axis of the expansion portion 20 (i.e., with respect to a cross-section taken along a plane that contains the central axis of the expansion portion and that is perpendicular to the plane of the paper). The second portion 26 and the first portion 22 are non-planar symmetric in that, for example, the cross-section of the first portion 22 is larger than the cross-section of the second portion 26. That is, the second portion 26 does not have a planar symmetric shape before and after being pulled out when being pulled out from the first portion 22 in the bent state and the front and the rear is reversed. Accordingly, by turning back the second portion 26, it is easy to obtain the bent state so that the first portion 22 and the second portion 26 do not contact each other. The non-planar symmetric arrangement helps make it easier for the expansion portion to turn back as illustrated in FIG. 4.

The portion 27 having the maximum outer diameter of the expansion portion 20 in the extended state is different from a portion having a maximum outer diameter in the bent state. Comparing FIG. 7 showing the extended state of the expansion portion 20 and FIG. 4 depicting the bent state of the expansion portion 20, the portion of the expansion portion 20 having the maximum outer diameter in the extended state is radially inward of the portion of the expansion portion 20 having the maximum outer diameter in the bent state.

The number of linear bodies 21 is, for example, but not limited to, 4 to 72. Moreover, the condition of the braiding of the linear bodies 21 is not particularly limited. An outer diameter of the linear bodies 21 can be appropriately selected depending on the material of the linear bodies 21 and the use of the expansion portion 20, which is, for example, 20 to 300 μm.

The constituent material from which the linear bodies 21 are fabricated is preferably a material having flexibility. For example, a shape memory alloy to which a shape memory effect and super elasticity is imparted by heating treatment, stainless, tantalum (Ta), titanium (Ti), silver (Pt), gold (Au), tungsten (W), polyolefin such as polyethylene and polypropylene, polyester such as polyamide and polyethylene terephthalate, fluorine-based polymer such as tetrafluoroethylene-ethylene copolymer (ETFE), polyether ether ketone (PEEK), polyimide, and the like can be suitably used. As a shape memory alloy, Ni—Ti-based alloys, Cu—Al—Ni-based alloys, Cu—Zn—Al-based alloys, or a combination of these alloys is preferably used. A structure in which a plurality of materials are combined includes, for example, a structure for imparting a radiopacity that a core wire made of Pt is covered with Ni—Ti alloy, or the core wire made of Ni—Ti alloy is subjected to gold plating.

The outer diameter of the outer tubes 52 and 62 is not particularly limited. For example, the outer diameter may be 0.3 to 3.0 mm. The inner diameter of the inner tubes 51 and 61 is not particularly limited. For example, the inner diameter may be 0.1 to 2.5 mm.

The constituent material from which the inner tubes 51 and 61 and the outer tubes 52 and 62 are fabricated is not particularly limited. For example, stainless steel and the like can be suitably used.

The maximum outer diameter of the expansion portion 20 in the bent state can be appropriately selected according to the inner diameter of the blood vessel to be treated. For example, the maximum outer diameter may be 1 to 40 mm. The outer diameter of the expansion portion 20 in the contracted state can be appropriately selected according to the inner diameter of the blood vessel to be treated. For example, the outer diameter may be 0.3 to 4.0 mm. The length of the expansion portion 20 in the bent state in the axial direction can be appropriately selected according to the blood vessel to be treated. For example, the length may be 20 to 150 mm.

As shown in FIGS. 3(A) and 3(B), the auxiliary expansion portion 80 has a plurality of wire portions 81 and a fixing portion 82 for fixing the plurality of wire portions 81 (proximal end portions of the wires 81) to the interlock shaft 87. The auxiliary expansion portion 80 can exhibit the strong fixing force in the blood vessel, and collect the object in the blood vessel. In a natural state in which the external force is not applied, the auxiliary expansion portion 80 is in the bent state in which the diameter of the auxiliary expansion portion 80 is expanded by the elastic force (restoring force) of the wire portions 81. In the bent state, the wire portions 81 expand to the outside in the radial direction from the center of the expansion toward the distal side. Moreover, the auxiliary expansion portion 80 is accommodated in the sheath 30 (see FIGS. 1 and 2), so that the auxiliary expansion portion 80 is in the contracted state in which the auxiliary expansion portion 80 is elastically deformed and the outer diameter of the auxiliary expansion portion 80 is reduced. The auxiliary expansion portion 80 and the distal side interlock portion 50 are interlocked with each other by the interlock shaft 87. Since the interlock shaft 87 is flexible, the expansion portion 20 and the auxiliary expansion portion 80 become easy to move independently. Accordingly, the expansion portion 20 and the auxiliary expansion portion 80 easily follow the shape of the blood vessel.

As shown in FIGS. 1 and 2, the sheath 30 includes a tubular body 31 (tube), a hub 32, and an anti-kink protector 33. The tubular body 31 includes a lumen 34 capable of accommodating the expansion tool 10. The distal end portion of the tubular e body 31 is curved. The tubular body 31 has a tubular body opening portion 36 at an end portion on the distal side. The tubular body opening portion 36 is inclined with respect to the central axis of the tubular body 31. Accordingly, the tubular body opening portion 36 has an opening area wider than the cross-sectional area of the lumen of the tubular body 31. That is, the opening area of the tubular body opening portion 36 is greater than the cross-sectional area of the lumen of the tubular body 31 at a cross-section perpendicular to the axis of the tubular body 31. Accordingly, the tubular body opening portion 36 can aspirate a wide range. The tubular body opening portion 36 faces toward the distal side since the tubular body 31 is curved. The hub 32 is fixed to the end portion on the proximal side of the tubular body 31. The hub 32 includes a hub opening portion 35 communicating with the lumen 34. The hub opening portion 35 can be interlocked with a Y connector 190 including a side tube 191. By interlocking with the Y connector 190, it is possible to communicate with a syringe 180 which generates negative pressure in a state where an elongated device (for example, shaft portion 24) is inserted into the hub opening portion 35. Moreover, by connecting the syringe 180 to the side tube 191 of the Y connector 190, it is possible to inject the thrombolytic agent into the lumen of the tubular body 31 from the syringe 180. The anti-kink protector 33 is a flexible member covering the interlocking portion of the tubular body 31 and the hub 32. The anti-kink protector 33 suppresses kinking of the tubular body 31.

The constituent material from which the tubular body 31 is fabricated is not particularly limited, but, for example, polyolefin such as polyethylene, polypropylene, ethylene-propylene copolymer, and ethylene-vinyl acetate copolymer, polyvinyl chloride, polystyrene, polyamide, and polyimide, and a combination thereof may be suitably used. The tubular body 31 may be formed of a plurality of materials, or a reinforcing member such as a wire may be embedded.

The pressing shaft 40 is a tubular body which can be accommodated in the lumen 34 of the sheath 30. The pressing shaft 40 has a t lumen 41 into which the shaft portion 24 of the expansion tool 10 can be inserted. The inner diameter of the lumen 41 is smaller than the outer diameter of the proximal side interlock portion 60 of the expansion tool 10. Accordingly, the proximal side interlock portion 60 cannot enter the lumen 41. Therefore, the proximal side interlock portion 60 can press against the distal side or distal end of the pressing shaft 40. Even without the pressing shaft 40, by pushing the shaft portion 24 itself or pulling the sheath 30 to the proximal side, the expansion portion 20 and the auxiliary expansion portion 80 can be pushed out from the sheath 30.

Next, an aspiration device 100 to be inserted into the blood vessel for removing a thrombus will be described.

Figure 8:
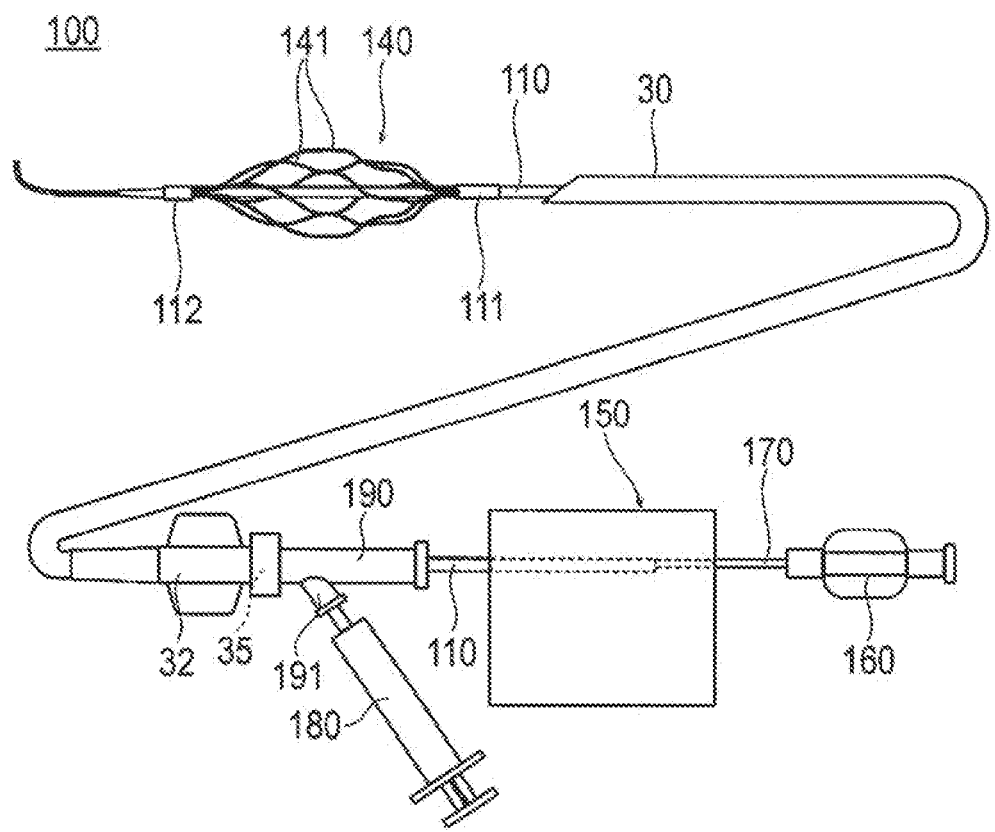
FIG. 8 is a plane view showing an aspiration device.

As shown in FIG. 8, the aspiration device 100 includes an elongated rotationally driven drive shaft 110, a slide portion 111 slidable with respect to the drive shaft 110, and a breaking member 140 rotated by the drive shaft 110. The aspiration device 100 further includes a rotationally driven portion 150 provided with a driving source (for example, motor) for rotating the drive shaft 110, a guide wire tubular body 170 into which the guide wire can be inserted, and a hub 160 provided at the proximal end portion of the guide wire tubular body 170. The aspiration device 100 further includes the sheath 30 capable of accommodating the drive shaft 110, the Y connector 190 configured to be interlocked with the hub opening portion 35 of the sheath 30, and the syringe 180 configured to be interlocked with the side tube 191 of the Y connector 190.

The proximal end portion of the drive shaft 110 is located at the rotationally driven portion 150. The drive shaft 110 can reciprocate along the circumferential direction by the rotationally driven portion 150. However, the drive shaft 110 is not limited to reciprocating, and it may rotate in one direction.

The guide wire tubular body 170 is provided in the hollow inside of the drive shaft 110 from the distal end portion to the hub 160. The guide wire tubular body 170 has a guide wire lumen into which a guide wire can be inserted.

The sheath 30 is a sheath used for the expansion tool 10. The sheath 30 is coaxially disposed on the outer side of the drive shaft 110. The lumen of the sheath 30 not only accommodates the breaking member 140 but functions as an aspiration lumen generating aspiration force under a negative pressure state. The sheath 30 can rotatably accommodate the drive shaft 110 via the Y connector 190. Moreover, by interlocking the side tube 191 of the Y connector 190 with the syringe 180, the lumen of the sheath 30 can be aspirated by the syringe 180 and can be brought into the negative pressure state. Moreover, by connecting the syringe 180 to the side tube 191, the thrombolytic agent can be injected into the lumen of the sheath 30 from the syringe 180. The thrombolytic agent entering the lumen of the sheath 30 is released from the opening portion on the distal side of the sheath 30.

The breaking member 140 is provided at the distal portion of the drive shaft 110. The breaking member 140 includes a plurality of (six in the present embodiment disclosed by way of example) wires 141. Each of the wires 141 is three-dimensionally curved, respectively. The number of wires 141 is not particularly limited. Each of the wires 141 is twisted in the same circumferential direction along the axial direction of the drive shaft 110. The proximal end portion of each of the wires 141 is fixed to the slide portion 111 which is slidable with respect to the drive shaft 110. The distal end portion of each of the wires 141 is fixed to a fixing portion 112 fixed to the drive shaft 110. The fixing position of each of the wires 141 with respect to the fixing portion 112 and the slide portion 111 is aligned in the circumferential direction. Moreover, a substantially center portion of each of the wires 141 curved in the axial direction is located radially outwardly of the drive shaft 110 and is aligned in the circumferential direction. Thereby, the breaking member 140 as a whole has a uniform bulging in the circumferential direction. When the drive shaft 110 rotates, the breaking member 140 also rotates accordingly, so that the thrombus in the blood vessel can be destroyed or the destroyed thrombus can be stirred. The breaking member may not only be a wire but also a laser cut pipe such as a stent.

The wires 141 constituting the breaking member 140 are constituted by metallic thin wires having flexibility. Until the drive shaft 110 is inserted into the target portion, the breaking member 140 is in a state accommodated in the inside of the sheath 30. After inserting the drive shaft 110 into the target portion, if the sheath 30 is slid to the proximal side with respect to the drive shaft 110, the breaking member 140 is exposed to the outside of the sheath 30 and expands. Accordingly, the wires 141 is desirably formed of a material having a shape memory property.

Figure 17:
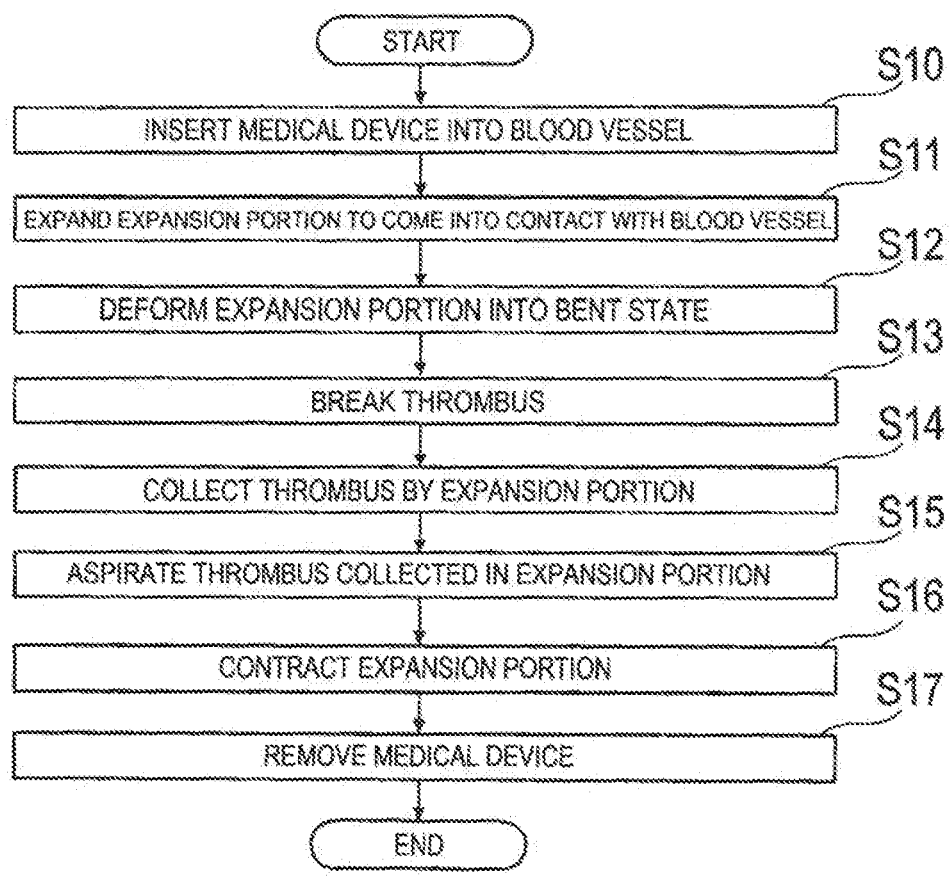
FIG. 17 is a flowchart for describing a procedure using the medical device.

Next, an example of a procedure and a method for using the medical device 1 and the aspiration device 100 according to the present embodiment will be described taking a case of aspirating and removing the thrombus (object) in the blood vessel (biological lumen) as an example with reference to the flowchart in FIG. 17.

First, on the upstream side (proximal side) of the blood vessel from a thrombus 300, an introducer sheath is percutaneously inserted into the blood vessel, and a guide wire 90 is inserted into the blood vessel via this introducer sheath. Next, the guide wire 90 is pushed forward until it reaches the distal side of the thrombus 300.

Next, as shown in FIG. 2, the medical device 1 in which breaking member expansion tool 10 and the pressing shaft 40 are accommodated in the sheath 30 is prepared. The Y connector 190 is connected to the hub 32 of the sheath 30. The expansion portion 20 and the auxiliary expansion portion 80 are disposed at a position near the distal end portion of the tubular body 31, with both the expansion portion 20 and the auxiliary expansion portion 80 being in the contracted state. The shaft portion 24 protrudes to the proximal side through the Y connector 190 from the hub opening portion 35 of the hub 32.

Next, the proximal end portion of the guide wire 90 (shown in FIGS. 9(A) and 9(B)) located outside the body is inserted into the guide wire lumens 54 and 64 (see FIG. 4) of the medical device 1. Then, as shown in FIG. 9(A), the medical device 1 is made to reach the distal side of the thrombus 300 by moving the medical device 1 along the guide wire 90 (step S10). Note that, in order to make the guide wire 90 reach the distal side of the thrombus 300, a support catheter prepared separately may be used.

Next, the sheath 30 is moved to the proximal side or in the proximal direction while suppressing movement of the pressing shaft 40 with a hand. At this time, the distal end portion of the pressing shaft 40 comes into contact with the proximal side interlock portion 60. Thereby, since the movement of the expansion portion 20 and the auxiliary expansion portion 80 is suppressed, the positions of the expansion portion 20 and the auxiliary expansion portion 80 in the blood vessel can be optionally adjusted. Then, by moving the sheath 30 to the proximal side with respect to the pressing shaft 40, the auxiliary expansion portion 80 and the auxiliary expansion portion 80 are sequentially released from the tubular body 31. Thereby, as shown in FIG. 9(B), first, the auxiliary expansion portion 80 is expanded by the restoring force of the auxiliary expansion portion, the plurality of wire portions 81 are widened our spread outwardly and come into contact with the intravascular wall surface (step S11). The wire portions 81 widen the blood vessel and bite into the blood vessel, so that the wire portions 81 are strongly fixed in position relative to the blood vessel.

When the expansion portion 20 is released from the tubular body 31, the proximal side interlock portion 60 moves in the distal direction so as to approach the distal side interlock portion 50. Then, the expansion portion 20 is expanded by the restoring force of the expansion portion, and comes into contact with the intravascular wall surface. At this time, the expansion portion 20 is in the extended state. The expansion portion 20 may be set in the boundary state or the bent state upon being released from the tubular body 31.

Figure 10A:
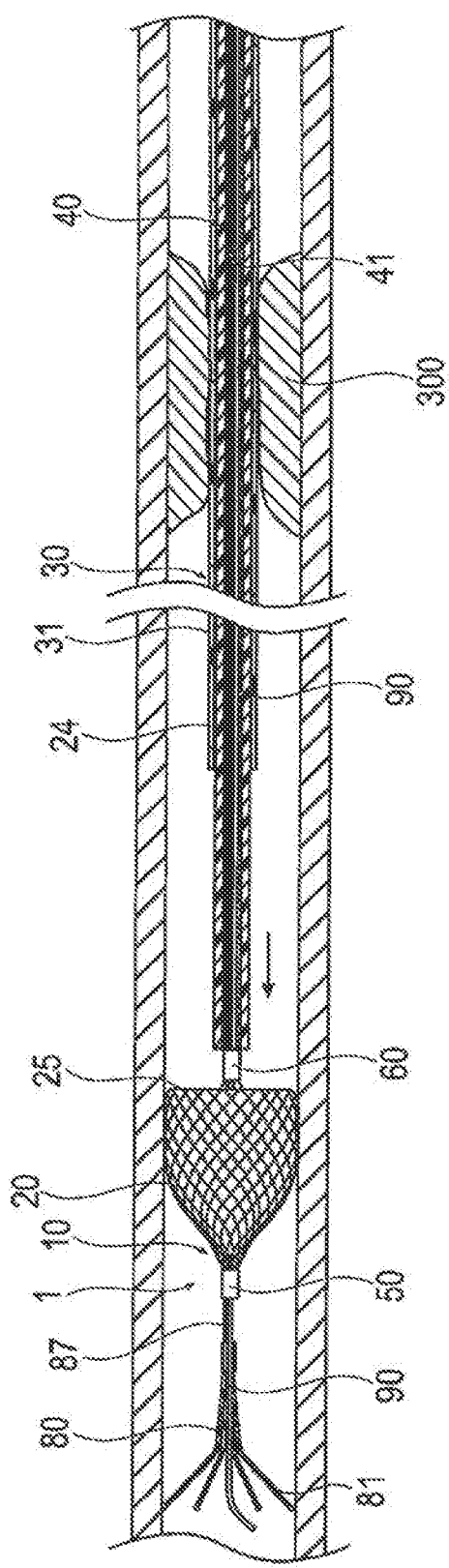
FIGS. 10(A) and 10(B) are cross-sectional views showing a state in the blood vessel, with FIG. 10(A) showing a state in which the expansion portion is indwelled in the blood vessel in the bent state, and FIG. 10(B) showing a state in which the aspiration device is inserted into the blood vessel.
Figure 11:
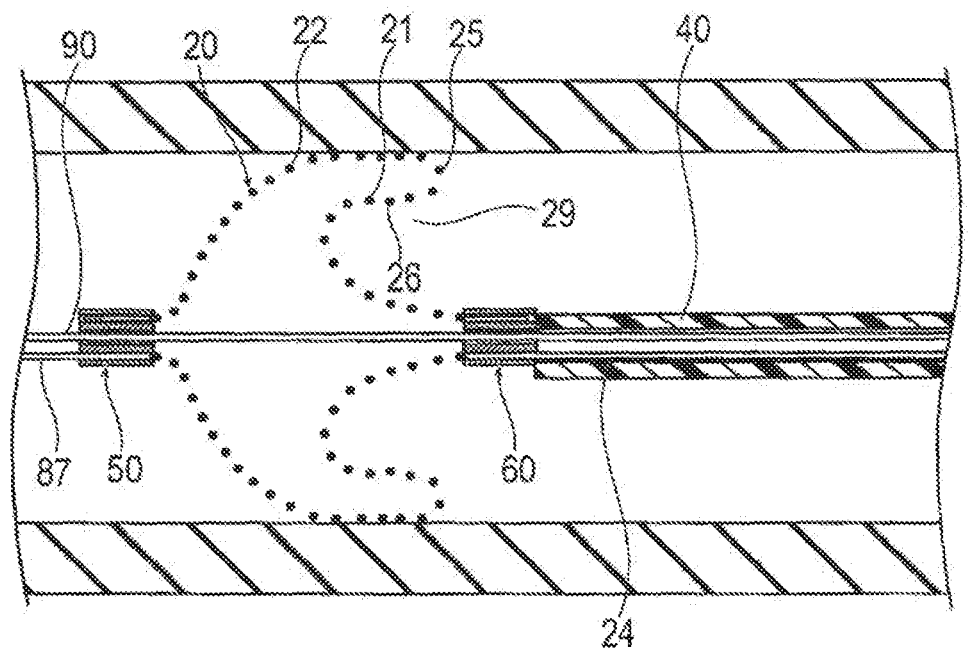
FIG. 11 is a cross-sectional view showing a state in which the expansion portion is indwelled in the blood vessel in the bent state.

Next, the pressing shaft 40 is moved to the distal side or in the distal direction, and the proximal side interlock portion 60 is pushed toward the distal side or in the distal direction by the distal end portion of the pressing shaft 40. Thereby, as shown in FIGS. 10(A) and 11, the expansion portion 20 is set in the bent state of being bent at the bent portion 25 (step S12). Since the expansion portion 20 is formed into a mesh shape, it bites into the intravascular wall surface and is strongly fixed. The expandable maximum diameter of the expansion portion 20 is larger than the inner diameter of the blood vessel into which the expansion portion 20 is inserted. Accordingly, the expansion portion 20 is brought into a state not completely expanded in the blood vessel, so that the expansion force is generated and the expansion portion 20 is effectively fixed to, and fixed in position relative to, the blood vessel wall.

When the expansion portion 20 is bent, the expansion portion 20 receives force in the distal direction. However, since the auxiliary expansion portion 80 is provided on the distal side of the expansion portion 20, the expansion portion 20 is supported by the auxiliary expansion portion 80 and can maintain the appropriate position. Even if the auxiliary expansion portion 80 receives force from the expansion portion 20 in the distal direction, the auxiliary expansion portion 80 hardly moves to the distal side or in the distal direction. Accordingly, when the expansion portion 20 is bent, the position of the expansion portion 20 can be appropriately maintained and the expansion portion 20 can be easily bent. Moreover, even when a strong force is applied from the blood stream, the auxiliary expansion portion 80 is strongly fixed relative to the blood vessel as described above, so that the auxiliary expansion portion 80 and the expansion portion 20 can be maintained at the appropriate positions.

Next, the pressing shaft 40 is removed from the living body leaving the sheath 30 in the living body. Since the expansion portion 20 is shaped into the bent state in advance, the bent state can be stably maintained.

Moreover, the expansion portion 20 and the auxiliary expansion portion 80 are interlocked with each other by the flexible interlock shaft 87, so that each position of the expansion portion 20 and the auxiliary expansion portion 80 can be appropriately maintained. Therefore, for example, even if the expansion portion 20 and the auxiliary expansion portion 80 are disposed at a portion curved in the blood vessel, an appropriate position can be maintained according to the shape of the blood vessel.

Figure 12:
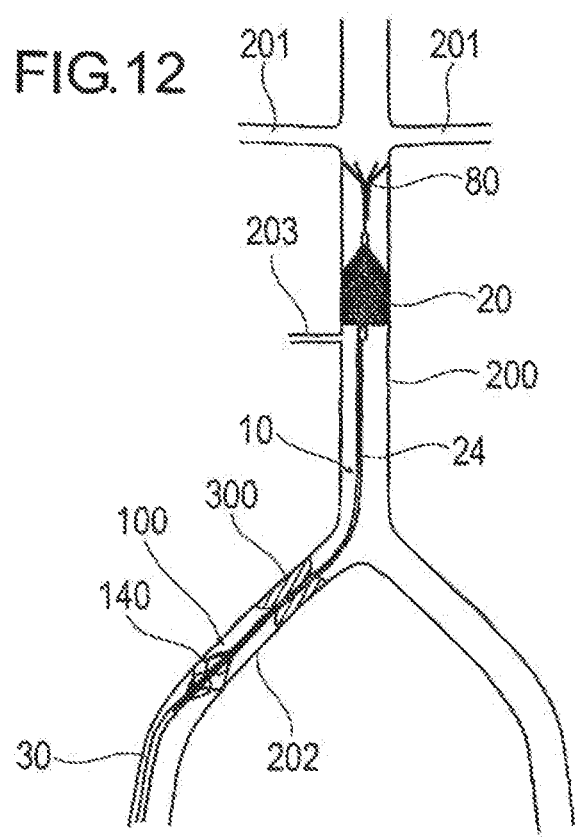
FIG. 12 is a schematic view showing the expansion tool in the blood vessel.

As shown in FIG. 12, it is preferable to locate the expansion portion 20 and the auxiliary expansion portion 80 in the bent state on the proximal side (lower leg side) from the merging portion of a renal vein 201 of a large vein 200. The thrombus 300 is located at, for example, an iliac vein 202. Thereby, it is possible to suppress a thrombus 301 fallen out from the thrombus 300 from flowing into the renal vein 201, and the safety is improved by suppressing the rise in renal pressure.

Figure 10B:
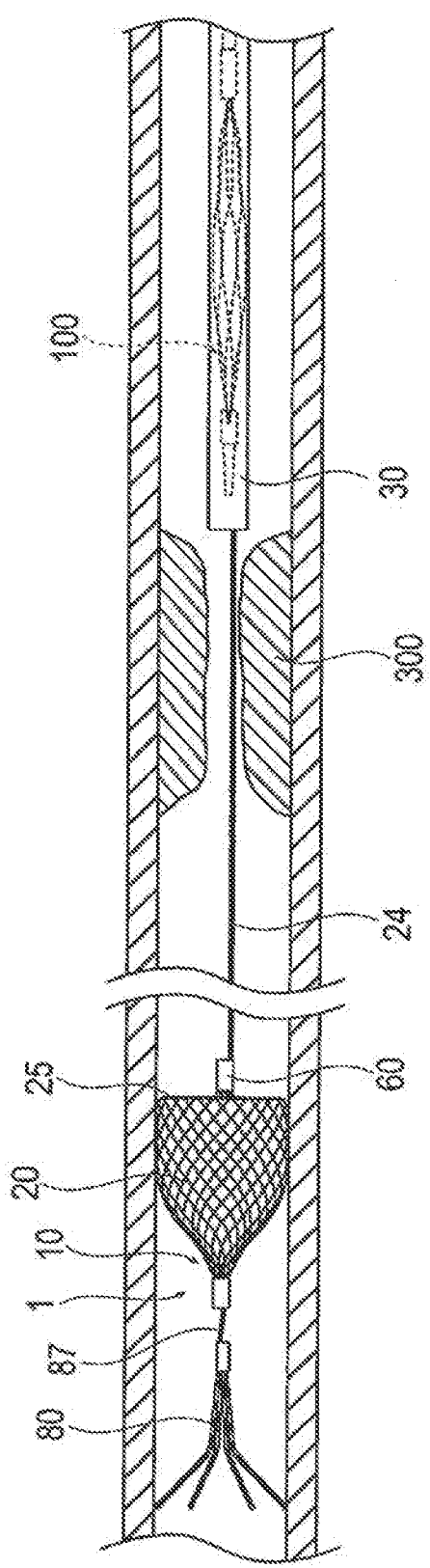

Next, the proximal end portion of the shaft portion 24 is inserted into the guide wire lumen of the aspiration device 100. Next, the distal portion of the drive shaft 110 including the breaking member 140 is inserted into the Y connector 190 connected with the sheath 30 with the shaft portion 24 as a guide. Then, as shown in FIG. 10(B), the drive shaft 110 is pushed forward and the aspiration device 100 is inserted into the proximal side of the thrombus 300. Thereafter, as shown in FIGS. 12 and 13(A), when the sheath 30 is moved to the proximal side, the breaking member 140 spreads in the blood vessel.

Next, in the state where the breaking member 140 is advanced to the vicinity of the thrombus 300, the drive shaft 110 is rotated by a rotationally driving portion 150. Thereby, as shown in FIG. 13(B), the breaking member 140 rotates and breaks the thrombus 300 while in a state of being stuck in the blood vessel (step S13).

When the breaking member 140 is rotated and moved to the axial direction in order to break the thrombus, as shown in FIG. 8, it is possible to connect the syringe 180, in which the thrombolytic agent is accommodated, with the side tube 191 on the hand-side of the sheath 30. Then, it is possible to push the plunger of the syringe 180 and eject the thrombolytic agent from the distal end portion of the sheath 30 simultaneously destroying the thrombus 300 by the breaking member 140. The ejection of the thrombolytic agent may be continuous or intermittent, and the ejection speed, and ejection amount may be optionally changed. In the case of intermittently ejecting the thrombolytic agent, it is possible to aspirate while the ejection is stopped. In addition, the thrombolytic agent may not be used. Moreover, when rotationally moving the breaking member 140 in the axial direction, the syringe 180 for aspiration can be connected to the side tube 191 on the hand-side of the sheath 30. Then, simultaneously destroying the thrombus 300 by the breaking member 140, it is possible to pull the plunger of the syringe 180 and aspirate the broken thrombus 301 by the sheath 30. During breaking, the thrombus 301 may not be aspirated.

As shown in FIG. 14, the thrombus 301 broken by the breaking member 140 reaches the expansion portion 20 located on the downstream side. The blood can pass through the expansion portion 20 through the gaps 21A. The first portion 22 and the second portion 26 are in a state in which the inner surfaces thereof are separated from each other without coming into contact with each other. The expansion portion 20 does not contact the bent portion 25. Accordingly, a space is formed between the first portion 22 and the second portion 26. Accordingly, the gaps 21A functioning as the filter of the expansion portion 20 can be satisfactorily maintained. Therefore, it is possible to appropriately maintain the blood flowing through the gaps 21A of the expansion portion 20, and reduce the burden on the living body. Moreover, the first portion 22 and the second portion 26 do not contact each other so that the range where the expansion portion 20 functions as a filter can be kept wide. That is, when the inner surfaces of the first portion 22 and the second portion 26 contact each other, the expansion portion 20 is brought into a collapsed state, so that the range where the blood can flow through from the outer surface to the inner surface of the expansion portion 20 can be reduced. On the other hand, when the range where the expansion portion 20 functions as a filter can be kept wide, the gaps 21A can be prevented from being clogged by the object.

In a case where the first portion 22 and the second portion 26 contact and come into contact with each other in the bent portion 25, apparently the gaps 21A of the mesh becomes small so that a thrombus 301 having a size equal to or smaller than the set size is captured. Thereby, the mesh tends to be clogged by the thrombus. On the other hand, since the expansion portion 20 is bent in a state in which the inner peripheral surfaces are separated from each other in the bent portion 25, the gaps 21A of the mesh is maintained, and the size for capturing the thrombus can be easily maintained. Accordingly, by being bent, the thrombus 301 can be satisfactorily collected (step S14).

The thrombus 301 that flowed through the fourth flow path S4 of the first portion 22 and passed through the expansion portion 20 doubled by being bent is further collected by the wire portions 81 functioning as a filter.

After the breaking of the thrombus 300 is completed, the reciprocation and the rotation of the drive shaft 110 are stopped. Thereafter, as shown in FIG. 16(A), the breaking member 140 is accommodated in the sheath 30, and the breaking member 140 is pulled out from the sheath 30. The state in which the Y connector 190 is connected to the hub 32 of the sheath 30 is maintained.

Next, the sheath 30 is moved to the distal side or in the distal direction along the shaft portion 24. Thereby, the pipe body opening portion 36 on the distal side of the sheath 30 is attached to the proximal side interlock portion 60 of the expansion portion 20. At this time, the tubular body 31 is curved, and the pipe body opening portion 36 is inclined with respect to the central axis of the tubular body 31. Accordingly, the pipe body opening portion 36 can be attached to the proximal side interlock portion 60 so as not to block the aspiration port as the proximal side interlock portion 60 enters the pipe body opening portion 36. Next, the syringe 180 for aspiration is connected to the Y connector 190 and the plunger of the syringe 180 is pulled to bring the inside of the sheath 30 into the negative pressure state. Thereby, the destroyed thrombus 301 can be aspirated from the pipe body opening portion 36 on the distal side of the sheath 30 and discharged to the syringe 180 (step S15). At this time, the proximal side interlock portion 60 is located on the proximal side from the bent portion 25. Accordingly, it is possible to effectively aspirate the thrombus 301 collected by the expansion portion 20 from the pipe body opening portion 36 attached to the proximal side interlock portion 60.

Moreover, since the filtering function of the expansion portion 20 can be satisfactorily maintained, the blood stream is secured. Accordingly, as shown in FIG. 12, even if a side branch 203 exists in the vicinity of the disposition positions of the expansion portion 20 and the auxiliary expansion portion 80, the thrombus 301 can hardly flow into the side branch 203 and the safety is improved.

As shown in FIG. 15, when the sheath 30 is moved to the distal side or in the distal direction along the shaft portion 24 in the state in which the sheath 30 is attached to the proximal side interlock portion 60, the proximal side interlock portion 60 approaches the distal side interlock portion 50. Thereby, a space between the first portion 22 and the second portion 26 is reduced. Then, the gaps 21A functioning as a filter are pulled out in the center direction (center direction of blood vessel) of the expansion portion 20 from the portion of the expansion portion 20 in contact with the blood vessel wall.

Accordingly, it is possible to improve the filtering function, for example, in a case where the gaps 21A of the expansion portion 20 are clogged and the filtering function is reduced and the like. Moreover, when the gaps 21A of the expansion portion 20 are clogged, the force in the distal direction that the second portion 26 receives from the blood is increased. Accordingly, the proximal side interlock portion 60 can be automatically moved so as to approach the distal side interlock portion 50 using the force received from the blood.

Then, when the thrombus 300 is broken and collected, aspirated, and removed by the expansion portion 20 and the auxiliary expansion portion 80, the positions of the expansion portion 20 and the auxiliary expansion portion 80 can be appropriately maintained by the auxiliary expansion portion 80. Accordingly, it is possible to appropriately perform the procedure of collecting, aspirating, and removing the thrombus 301.

After the aspiration of the thrombus 301 by the sheath 30 is completed, the sheath 30 is pushed into the distal side or in the distal direction as shown in FIG. 16(B). At this time, the shaft portion 24 can be pulled to the proximal side. Thereby, the proximal side interlock portion 60 enters the inside of the sheath 30 as being separated from the distal side interlock portion 50. Then, the expansion portion 20 is brought into the contracted state from the bent state, and accommodated in the inside of the sheath 30 (step S16). Furthermore, the auxiliary expansion portion 80 is also reduced in the diameter and accommodated in the sheath 30. When the expansion portion 20 and the auxiliary expansion portion 80 are accommodated in the inside of the sheath 30, since the thrombus 301 attached to these can be also accommodated in the sheath 30, the safety is increased.

After accommodating the expansion portion 20 and the auxiliary expansion portion 80 in the inside of the sheath 30, the expansion tool 10 is removed from the blood vessel with the sheath 30 to complete the procedure (step S17).

As described above, the medical device 1 according to the present embodiment is a device to be inserted into the blood vessel (biological lumen) for collecting the thrombus 301 (object) in the blood vessel, and includes the elongated shaft portion 24 and the expansion portion 20 which is an elastically deformable cylindrical body having the plurality of gaps 21A and in which at least one of the proximal portion and the distal portion of the cylindrical body is interlocked with the shaft portion 24, in which the expansion portion 20 has the ring-shaped bent portion 25 which protrudes toward a proximal side position radially outside the expansion portion 20 in a bent state of being bent along an axial direction, and the axial length of the second portion 26 from the bent portion 25 to the proximal end of the expansion portion 25 is shorter than the axial length of the first portion 22 from the bent portion 25 to the distal end of the expansion portion 20. When the expansion portion 20 is in any of the natural state, bent state, boundary state, extended state, and contracted state, the axial length of the second portion 26 is shorter than the axial length of the first portion 22. When the medical device 1 configured as described above is in the bent state, the first portion 22 and the second portion 26 hardly contact each other and a space is formed between the first portion 22 and the second portion 26. Accordingly, it is possible to appropriately maintain the gaps 21A of the expansion portion 20 and to effectively collect the thrombus 301 by the expansion portion 20 by suppressing the clogging.

Moreover, in the extended state in which the second portion 26 is moved to the proximal side with respect to the first portion 22 and pulled out from the inside of the first portion 22, the shapes of the first portion 22 and the second portion 26 are non-planar symmetric with respect to the axially orthogonal cross section (i.e., with respect to a cross-section taken along a plane that contains the central axis of the expansion portion and that is perpendicular to the plane of the paper). The second portion 26 and the first portion 22 are non-planar symmetric in that the cross-section of the first portion 22 is larger than the cross-section of the second portion 26. Thereby, when brought into the bent state, the first portion 22 and the second portion 26 hardly contact each other, so that a space is easily formed between the first portion 22 and the second portion 26.

Moreover, since the expansion portion 20 is shaped in advance, it is in the bent state in the natural state. That is, the expansion portion 20 is in the bent state when no external or outside force is applied to the expansion portion. Accordingly, it is easy to set so as to have an optimum shape in the bent state. Therefore, the shape of the expansion portion 20 is stabilized in the bent state, and the thrombus 301 can be effectively collected.

Moreover, in the extended state, the second portion 26 has an outer diameter larger than the first portion 22. Thereby, in the extended state, since the second portion 26 and the first portion 22 have different shapes, by obtaining the bent state, a space is easily formed between the first portion 22 and the second portion 26. Accordingly, it is possible to appropriately maintain the gaps 21A of the expansion portion 20 and to effectively collect the thrombus 301 by the expansion portion 20 by suppressing the clogging.

Moreover, the first portion 22 and the second portion 26 are separately located without coming into contact with each other in the bent state. Thereby, since a space is formed between the first portion 22 and the second portion 26 when it is brought into the bent state, it is possible to appropriately maintain the gaps 21A of the expansion portion 20 and to effectively collect the thrombus 301 by the expansion portion 20 by suppressing the clogging.

Moreover, in the boundary state at the time when entire second portion 26 is pulled out from the inside of the first portion 22 in the bent state, the axes of the linear bodies 21 located in the second portion 26 have the inflection points P on a plane seen from the axial direction of the expansion portion 20. Thereby, it is possible to turn back the expansion portion 20 using the portion having the inflection points P of the linear bodies 21. Accordingly, the shape of the expansion portion 20 in the bent state is stabilized, and the bent state can be easily obtained.

Moreover, in the bent state, the relative axial position of the second portion 26 with respect to the first portion 22 can be changed by the expansion portion 20. Thereby, when the gaps 21A are clogged in the biological lumen, the second portion 26 is moved with respect to the first portion 22, and it is possible to increase a portion having the gaps 21A of the expansion portion 20 which are not clogged.

Moreover, in the expansion portion 20 in the extended state, the length from the portion 27 having the maximum outer diameter of the expansion portion 20 to the distal end portion is longer than the length from the portion 27 having the maximum outer diameter of the expansion portion 20 to the proximal end portion. Thereby, since the axial length of the second portion 26 is shorter than the first portion 22, a space is easily formed between the first portion 22 and the second portion 26 by obtaining the bent state. Accordingly, it is possible to appropriately maintain the gaps 21A of the expansion portion 20 and to effectively collect the thrombus 301 by the expansion portion 20 by suppressing the clogging.

Moreover, in the extended state, the maximum inclination angle of the second portion 26 with respect to the axial direction is larger than the maximum inclination angle of the first portion 22 with respect to the axial direction. Accordingly, the second portion 26 tends to be bent in the axial direction and to be located in the inside of the first portion 22. Furthermore, since the first portion 22 and the second portion 26 have different shapes by obtaining the bent state, a space is easily formed between the first portion 22 and the second portion 26. Accordingly, it is possible to appropriately maintain the gaps 21A of the expansion portion 20 and to effectively collect the thrombus 301 by the expansion portion 20 by suppressing the clogging.

Moreover, in the bent state, the curvature radius r1 of the portion convex toward the distal side of the first portion 22 is larger than the curvature radius r2 of the portion convex toward the distal side of the second portion 26. Accordingly, the second portion 26 tends to be bent in the axial direction and to be located in the inside of the first portion 22. Furthermore, since the first portion 22 and the second portion 26 have different shapes by obtaining the bent state, a space is easily formed between the first portion 22 and the second portion 26. Accordingly, it is possible to appropriately maintain the gaps 21A of the expansion portion 20 and to effectively collect the thrombus 301 by the expansion portion 20 by suppressing the clogging.

Moreover, the present invention also includes a procedure or method for aspirating and removing the thrombus 301 (object) formed in the lesion area in the blood vessel (biological lumen) using the aforementioned medical device 1. The procedure method includes step S10 of inserting the sheath 30 in which the expansion portion 20 is accommodated into the blood vessel, step S11 of pushing out the expansion portion 20 from the sheath 30 in the blood vessel and expanding the expansion portion 20 by the elastic force of the expansion portion to be brought into contact with the blood vessel, step S12 of causing the expansion portion 20 into the bent state, and step S14 of collecting the thrombus 301 in the blood vessel by the expansion portion 20. In the procedure configured as described above, when the expansion portion 20 is set in the bent state, the first portion 22 and the second portion 26 hardly contact each other so that a space is formed between the first portion 22 and the second portion 26. Accordingly, it is possible to appropriately maintain the gaps 21A of the expansion portion 20 and to effectively collect the thrombus 301 by the expansion portion 20 by suppressing the clogging.

The present invention is not limited only to the embodiments described above, and various modifications are possible by those skilled in the art within the technical idea of the present invention. For example, in the present embodiment, the medical device 1 has a structure to be accessed from the upstream side of the target lesion, but it may have a structure to be accessed from the downstream side of the target lesion.

Moreover, in the present embodiment, the device inserted into the blood vessel along the shaft portion 24 is the aspiration device 100 including the breaking member 140. However, the configuration of the device to be inserted is not limited as long as the object can be aspirated from the blood vessel. Moreover, the device for aspirating an object in the blood vessel may be configured separated from the device for dropping the object from the blood vessel. Therefore, the device for aspirating an object in the blood vessel may be a pipe body capable of performing aspiration without a breaking member. For example, only the sheath 30 may be a device for aspirating an object. Moreover, the sheath 30 is used in both the medical device 1 and the aspiration device 100, but a separated sheath may be used for each device. Moreover, an aspiration device and a breaking device may not be provided.

Moreover, the biological lumen into which the medical device 1 is inserted is not limited to the blood vessel, and may be, for example, a vessel, a ureter, a bile duct, an oviduct, a hepatic duct, and the like.

Moreover, the configuration of the auxiliary expansion portion is not particularly limited. Moreover, the medical device may not include an auxiliary expansion portion.

Figure 18:
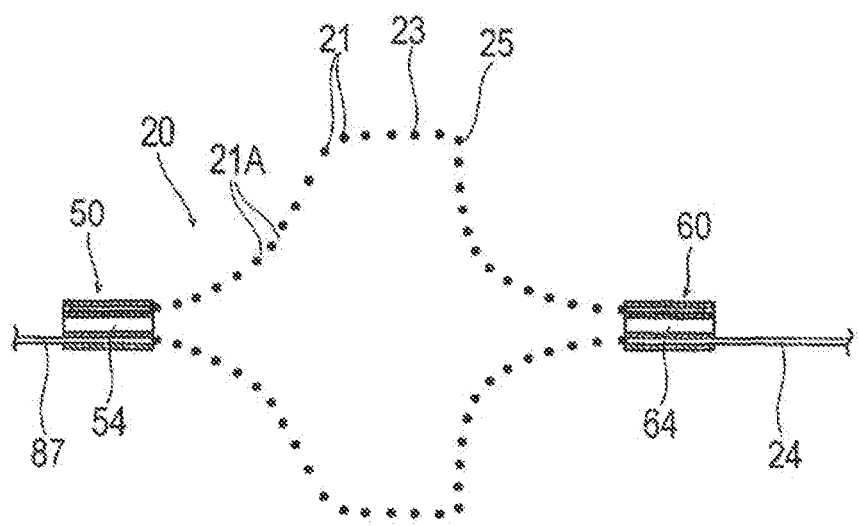
FIG. 18 is a cross-sectional view showing a modification example of the medical device according to the embodiment.

Moreover, in the modification example as shown in FIG. 18, the expansion portion 20 may have a straight portion 23 having a constant outer diameter in the axial direction in the boundary state. The straight portion 23 is located in the first portion 22. Thereby, the straight portion 23 may come into contact with the intravascular wall surface in a wide range (i.e., the length or area of contact between the straight portion 23 of the expansion portion 20 and the intravascular wall surface is enlarged). Accordingly, the expansion portion 20 is hardly inclined in the blood vessel, and a good position can be maintained.

Figure 19:
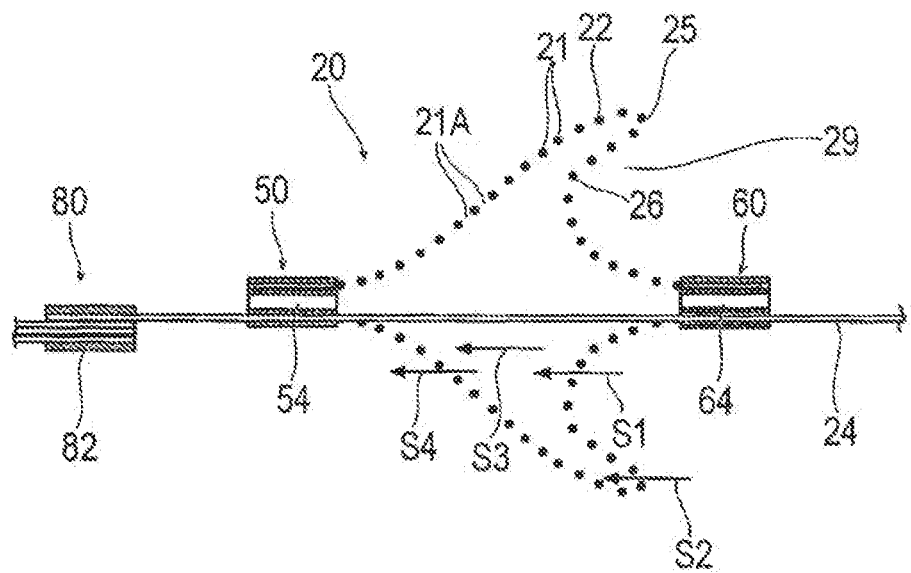
FIG. 19 is a cross-sectional view showing another modification example of the medical device according to the embodiment.

Moreover, in another modification example shown in FIG. 19, the shaft portion 24 may pass through the expansion portion 20 from the hand and extend up to the auxiliary expansion portion 80. The shaft portion 24 slidably passes through the proximal side interlock portion 60. The shaft portion 24 is interlocked with the distal side interlock portion 50. Furthermore, the distal end portion of the shaft portion 24 is interlocked with the fixing portion 82 of the auxiliary expansion portion 80. Being interlocked with the shaft portion 24 is not limited to being fixed to the shaft portion 24, and includes being interlocked to be relatively rotatable and movable.

Moreover, a flexible film member for restricting blood flow may be fixed at the portion of the expansion portion 20.

Figure 20:
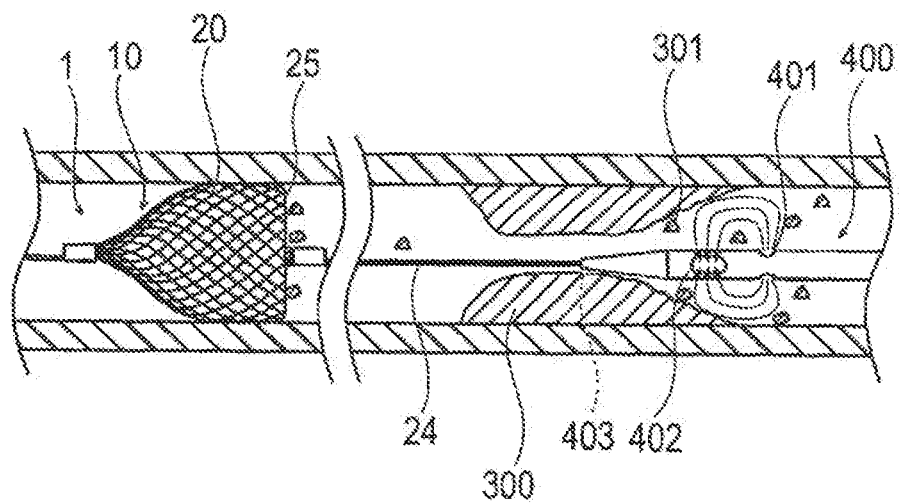
FIG. 20 is a cross-sectional view showing another using method of the medical device according to the embodiment.

Moreover, as shown in FIG. 20, as another method of use (procedure) using the medical device 1, the medical device 1 may be used with device 400 which ejects liquid to destroy the thrombus 300. The device 400 includes a release port 401 for discharging liquid, an aspiration port 402 aspirating the liquid, and a guide wire lumen 403. The aspiration port 402 is provided on the distal side of the release port 401, but may be provided on the proximal side. The release port 401 can release liquid supplied from the proximal portion of the device 400. The aspiration port 402 can aspirate liquid or an object by the negative pressure supplied from a syringe and the like connected to the proximal portion of the device 400.

When using the medical device 1, similarly to the aforementioned using method, the expansion portion 20 is expanded on the distal side from the thrombus 300 in the blood vessel and brought into the bent state (see FIGS. 9 and 10). Next, the sheath 30 and the pressing shaft 40 are removed. Next, the proximal end of the shaft portion 24 is inserted into the guide wire lumen 403 of the device 400. Next, the device 400 is made to reach the vicinity of the thrombus 300 along the shaft portion 24. Thereafter, the liquid is released from the release port 401. The released liquid destroys the thrombus 300. The destroyed thrombus 301 is aspirated and discharged from the aspiration port 402 with the released liquid and the blood. There are cases in which the destroyed thrombus 301 is not aspirated by the aspiration port 402. The not aspirated thrombus 301 flows with the blood and is collected by the expansion portion 20. The collected thrombus 301 is finally aspirated by the aspiration port 402 of the device 400 that reaches the vicinity of the expansion portion 20. After the thrombus 300 is destroyed, aspirated, and removed, the device 400 is removed from the blood vessel. Next, the sheath 30 is inserted into the blood vessel, and the expansion portion 20 is contracted and accommodated in the sheath 30. Thereafter, the expansion tool 10 is removed from the blood vessel with the sheath 30, and the procedure is completed. Note that, the device 400 may include a balloon or mesh-like tubular member that can be expanded radially outward.

In the bent state, at least one of the release port 401 and the aspiration port 402 of the device 400 may be located at the inner space 29 on the inner side of the concave-shaped second portion 26. In this case, the thrombus 301 collected by the inner space 29 is floating in the inner space 29 by the liquid released from the release port 401. Thereafter, as the thrombus 301 floats, it becomes easier for the aspiration port 402 to aspirate the thrombus.

The detailed description above describes embodiments of a medical device and procedure representing examples of the inventive medical device and procedure disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device to be inserted into a biological lumen for collecting an object in the biological lumen, the medical device comprising:
    an elongated shaft possessing a distal end portion;
    an expansion portion that includes an elastically deformable body, the elastically deformable body possessing a proximal portion and a distal portion, the elastically deformable body including a plurality of through gaps that pass through the elastically deformable body;
    the proximal portion of the elastically deformable body being interlocked with a proximal side interlock portion, the proximal side interlock portion including a lumen extending throughout the proximal side interlock portion, the proximal side interlock portion being fixed to the distal end portion of the elongated shaft so that the elongated shaft and the proximal side interlock portion move together as a unit whereby movement of the elongated shaft results in movement of the proximal side interlock portion, the elongated shaft extending away from the elastically deformable body in a proximal direction;
    the proximal side interlock portion including an inner tube and an outer tube, the distal portion of the elongated shaft being fixed to at least one of the inner tube of the proximal side interlock portion and the outer tube of the proximal side interlock portion;
    the expansion portion including, when the expansion portion is in a bent state, a radially outwardly located annular-shaped portion that is bent toward the proximal direction;
    the expansion portion being changeable between the bent state and an extended state, the expansion portion in the bent state including a first portion and a second portion, the second portion being located inside the first portion when the expansion portion is in the bent state, and the second portion moving in the proximal direction with respect to the first portion and being pulled out from the inside of the first portion when the expansion portion changes from the bent state to the extended state.

2. The medical device according to claim 1, wherein the distal end portion of the elongated shaft is positioned between the inner tube of the proximal side interlock portion and the outer tube of the proximal side interlock portion.

3. The medical device according to claim 1, wherein the lumen passing through the proximal side interlock portion is a centrally located guide wire lumen into which a guide wire is insertable.

4. The medical device according to claim 1, wherein the distal portion of the elastically deformable body is interlocked with a distal side interlock portion.

5. A medical device to be inserted into a biological lumen for collecting an object in the biological lumen, the medical device comprising:
    an elongated shaft possessing a distal end portion;
    an expansion portion that includes an elastically deformable body, the elastically deformable body possessing a proximal portion and a distal portion, the elastically deformable body including a plurality of through gaps that pass through the elastically deformable body;
    the proximal portion of the elastically deformable body being interlocked with a proximal side interlock portion;
    the distal end portion of the elongated shaft being fixed in place relative to the elastically deformable body by way of the proximal side interlock portion so that the elongated shaft and the proximal side interlock portion move together as a unit whereby movement of the elongated shaft results in movement of the proximal side interlock portion, the elongated shaft extending away from the elastically deformable body in a proximal direction;
    the expansion portion including, when the expansion portion is in a bent state, a radially outwardly located annular-shaped portion that is bent toward the proximal direction;
    the expansion portion being changeable between the bent state and an extended state, the expansion portion in the bent state including a first portion and a second portion, the second portion being located inside the first portion when the expansion portion is in the bent state, and the second portion moving in the proximal direction with respect to the first portion and being pulled out from the inside of the first portion when the expansion portion changes from the bent state to the extended state; and
    the elongated shaft being the only elongated shaft that is fixed in place relative to the elastically deformable body and that also extends away from the elastically deformable body in the proximal direction.

6. The medical device according to claim 5, wherein the elongated shaft is a first elongated shaft, and further comprising a second elongated shaft having a proximal end portion, the proximal end portion of the second elongated shaft being fixed in place relative to the elastically deformable body, the second elongated shaft extending away from the elastically deformable body in a distal direction that is opposite the proximal direction.

7. The medical device according to claim 5, wherein the distal portion of the elastically deformable body is interlocked with a distal side interlock portion.

8. The medical device according to claim 7, wherein the elongated shaft is a first elongated shaft, and further comprising a second elongated shaft having a proximal end portion, the proximal end portion of the second elongated shaft being fixed in place relative to the elastically deformable body by way of the distal side interlock portion so that the second elongated shaft and the distal side interlock portion move together as a unit.

9. The medical device according to claim 5, wherein the distal end portion of the elongated shaft is a distal-most end of the elongated shaft that is fixed to the proximal side interlock portion.

10. The medical device according to claim 5, wherein the distal portion of the elastically deformable body is interlocked with a distal side interlock portion, the proximal side interlock portion and the distal side interlock portion being axially spaced apart by a first axial distance when the expansion portion is in the extended state and being axially spaced apart by a second axial distance when the expansion portion is in the bent state, the first axial distance being greater than the second axial distance.

11. The medical device according to claim 5, wherein the proximal side interlock portion includes an inner tube and an outer tube.

12. The medical device according to claim 11, wherein the distal end portion of the elongated shaft is positioned between the inner tube of the proximal side interlock portion and the outer tube of the proximal side interlock portion.

13. A medical device to be inserted into a biological lumen for collecting an object in the biological lumen, the medical device comprising:

an elongated shaft possessing a distal end portion;

an expansion portion that includes an elastically deformable body having a plurality of through gaps that pass through the elastically deformable body, the expansion portion possessing a proximal portion and a distal portion;

the proximal portion of the expansion portion being interlocked with a proximal side interlock portion, the proximal side interlock portion including an outer tube and an inner tube, the inner tube being positioned inside the outer tube;

the distal end portion of the elongated shaft being fixed to at least one of the inner tube of the proximal side interlock portion and the outer tube of the proximal side interlock and extending away from the expansion portion in a proximal direction;

the expansion portion being changeable from an extended state to a bent state by a restoring force of the expansion portion and without application of any forces external to the expansion portion so that as the expansion portion changes form from the extended state to the bent state, the expansion portion expands radially outwardly and an axial distance between the distal portion of the expansion portion and the proximal portion of the expansion portion is reduced;

the expansion portion including, when the expansion portion is in the bent state, a radially outwardly located annular-shaped portion that is bent toward the proximal direction; and the expansion portion in the bent state including a first portion and a second portion, the second portion being located inside the first portion when the expansion portion is in the bent state, the expansion portion being changeable from the bent state to the extended state, and the second portion moving in the proximal direction with respect to the first portion and being pulled out from the inside of the first portion when the expansion portion changes from the bent state to the extended state.

14. The medical device according to claim 13, wherein the distal end portion of the elongated shaft is positioned between the inner tube of the proximal side interlock portion and the outer tube of the proximal side interlock portion.

15. The medical device according to claim 13, wherein the proximal side interlock portion incudes a lumen passing through the proximal side interlock portion.

16. The medical device according to claim 13, wherein the distal portion of the expansion portion is interlocked with a distal side interlock portion.

\* \* \* \* \*